US008361472B2

(12) United States Patent
Lin et al.

(10) Patent No.: US 8,361,472 B2
(45) Date of Patent: *Jan. 29, 2013

(54) ANTI-PSGL-1 ANTIBODIES

(75) Inventors: Rong-Hwa Lin, Palo Alto, CA (US); Chung Nan Chang, Foster City, CA (US); Pei-Jiun Chen, Taipei (TW); Chiu-Chen Huang, Taipei (TW)

(73) Assignee: AbGenomics Cooperatief U.A., Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 12/858,110

(22) Filed: Aug. 17, 2010

(65) Prior Publication Data
US 2011/0172397 A1 Jul. 14, 2011

Related U.S. Application Data

(63) Continuation of application No. 12/399,516, filed on Mar. 6, 2009, now abandoned, which is a continuation of application No. 11/125,837, filed on May 10, 2005, now Pat. No. 7,604,800.

(60) Provisional application No. 60/569,892, filed on May 10, 2004.

(51) Int. Cl.
*A61K 39/395* (2006.01)
*C07K 16/28* (2006.01)

(52) U.S. Cl. ............... 424/154.1; 424/130.1; 424/133.1; 424/141.1; 424/143.1; 424/144.1; 424/152.1; 424/153.1; 424/172.1; 424/173.1; 530/387.1; 530/387.3; 530/388.1; 530/388.2; 530/388.22; 530/388.7; 530/388.73; 530/388.75

(58) Field of Classification Search .................. None
See application file for complete search history.

(56) References Cited

U.S. PATENT DOCUMENTS

| 5,378,464 | A | 1/1995 | McEver |
| 5,618,785 | A | 4/1997 | Heavner et al. |
| 5,709,859 | A | 1/1998 | Aruffo et al. |
| 5,710,123 | A | 1/1998 | Heavner et al. |
| 5,808,025 | A | 9/1998 | Tedder et al. |
| 5,827,817 | A | 10/1998 | Larsen et al. |
| 5,834,425 | A | 11/1998 | Tedder et al. |
| 5,840,679 | A | 11/1998 | Larsen et al. |
| 5,843,707 | A | 12/1998 | Larsen et al. |
| 5,852,175 | A | 12/1998 | Cummings et al. |
| 5,866,124 | A | 2/1999 | Hardman et al. |
| 5,972,625 | A | 10/1999 | Rosen et al. |
| 6,056,956 | A | 5/2000 | Cobbold et al. |
| 6,124,267 | A | 9/2000 | McEver et al. |
| 6,177,547 | B1 | 1/2001 | Cummings et al. |
| 6,210,671 | B1 | 4/2001 | Co |
| 6,309,639 | B1 | 10/2001 | Cummings et al. |
| 6,348,581 | B1 | 2/2002 | Anderson et al. |
| 6,506,382 | B2 | 1/2003 | Cummings et al. |
| 6,667,036 | B2 | 12/2003 | Cummings et al. |
| 6,884,619 | B2 | 4/2005 | Hockfield et al. |
| 7,387,777 | B2 | 6/2008 | Wagner et al. |
| 7,604,800 | B2 * | 10/2009 | Lin et al. ............ 424/154.1 |
| 7,744,888 | B2 | 6/2010 | Lin et al. |
| 2002/0058034 | A1 | 5/2002 | Manjunath et al. |
| 2002/0164336 | A1 | 11/2002 | Harrison et al. |
| 2003/0049252 | A1 * | 3/2003 | Lin et al. ............ 424/144.1 |
| 2004/0001839 | A1 * | 1/2004 | Levanon et al. ......... 424/178.1 |
| 2004/0002450 | A1 * | 1/2004 | Lazarovits et al. .......... 514/12 |
| 2004/0116333 | A1 | 6/2004 | Lin et al. |
| 2005/0266003 | A1 | 12/2005 | Lin et al. |
| 2006/0003940 | A1 | 1/2006 | Lin et al. |
| 2009/0191204 | A1 | 7/2009 | Lin et al. |
| 2009/0198044 | A1 | 8/2009 | Lin et al. |
| 2009/0304709 | A1 | 12/2009 | Lin et al. |
| 2010/0080819 | A1 | 4/2010 | Lin et al. |
| 2011/0178270 | A1 | 7/2011 | Lin et al. |

FOREIGN PATENT DOCUMENTS

| CN | 1473052 A | 2/2004 |
| WO | WO 97/06176 A2 | 2/1997 |
| WO | WO 00/25808 A1 | 5/2000 |
| WO | 01/83806 A1 | 11/2001 |
| WO | 02/053700 A2 | 7/2002 |
| WO | WO 03/013603 A1 | 2/2003 |
| WO | WO 2005/110475 A2 | 11/2005 |

OTHER PUBLICATIONS

International Search Report and Written Opinion for PCT/US2005/016357 mailed on Nov. 3, 2005.
GenBank Accession No. AAA38463, downloaded Nov. 2, 2009.
GenBank Accession No. AAH29782, Selectin P ligand [*Homo sapiens*], originally posted May 20, 2002.
GenBank Accession No. AAO19056, downloaded Nov. 2, 2009.
GenBank Accession No. AAQ74699, downloaded Nov. 2, 2009.
GenBank Submission; Database EMBL, Accession No. AF045490; O'Conner et al.; first submitted to EMBL Feb. 2, 1998; 2 pages.
[No Author Listed] BLAST (Basic Local Alignment Search Tool). Accession No. AAH03874: Selectin, platelet (p-selectin) ligand.. Last accessed on Apr. 27, 2010 at http://blast.ncbi.nlm.nih.gov/Blast.cgi . 4 pages.
[No Author Listed] CD162 (PL1). Monoclonal Antibody. Medical & Biological Laboratories Co., Ltd. May 31, 2002. 2 pages.
[No Author Listed] CD162 (PL2). Monoclonal Antibody. Medical & Biologicals Laboratories Co., Ltd. May 31, 2002. Last accessed online Oct. 6, 2011 at ://www.mblintl.com/sites/default/files/datasheets/K0037-3.pdf. 1 page.
[No Author Listed] Product details for anti-CD162/PSGL-1 (clone PL2) antibody. Antibodies-online.com. 3 pages. Last accessed online Jul. 1, 2011 at http://www.antibodies-online.com/productsheets/en/ABIN131576.pdf.
[No Author Listed] Purified Mouse Anti-Human CD162. Technical Data Sheet. BD Pharmingen. 2006. 2 pages.
[No Author Listed] Safety, Tolerability, Pharmacokinetics and Pharmacodynamics of Single Doses of AbGn-168 in Psoriasis. Sponsored by Boehringer Ingelheim Pharmaceuticals. Last accessed on Aug. 28, 2009 at //clinicaltrials.gove/ct2/show/NCT00848055?cond=psoriasis&spons . . . Study Start Date: Dec. 2008. 3 pages.

(Continued)

*Primary Examiner* — Phillip Gambel

(74) *Attorney, Agent, or Firm* — Wolf, Greenfield & Sacks, P.C.

(57) ABSTRACT

Immunoglobulin chains or antibodies having light or heavy chain complementarity determining regions of antibodies that bind to P-Selectin Glycoprotein Ligand-1. Also disclosed are methods of inducing death of an activated T-cell and of modulating a T cell-mediated immune response in a subject.

4 Claims, No Drawings

OTHER PUBLICATIONS

Battistini et al., CD8+ T cells from 1-37 patients with acute multiple sclerosis display selective increase of adhesiveness in brain venules: A critical role for P-selectin glycoprotein ligand-1. Blood. Jun. 15, 2003;101(12):4775-82. Epub Feb. 20, 2003.

Beckwith et al., The protein product of the proto-oncogene c-cbl forms a complex with phosphatidylinositol 3-kinase p85 and CD19 in anti-igm stimulated human B-lymphoma cells. Blood. Nov. 1, 1996;88(9):3502-7.

Besnault et al., B cell receptor cross-linking triggers a caspase-8-dependent apoptotic pathway that is independent of the death effector domain of Fas-associated death domain protein. J Immunol. Jul. 15, 2001;167(2):733-40.

Borges et al., P-selectin glycoprotein ligand-1 (PSGL-1) on T helper 1 but not on T helper 2 cells binds to P-selectin and supports migration into inflamed skin. J Exp Med. Feb. 3, 1997;185(3):573-8.

Borges et al., The binding of T cell-expressed P-selectin glycoprotein ligand-1 to E- and P-selectin is differentially regulated. J Biol Chem. Nov. 7, 1997;272(45):28786-92.

Chen et al., Cross-linking of P-selectin glycoprotein ligand-1 induces death of activated T cells. Blood. Nov. 15, 2004;104(10):3233-42. Epub Jun. 15, 2004.

Co et al,, Chimeric and humanized antibodies with specificity for the CD33 antigen. J Immunol. Feb. 15, 1992;148(4):1149-54.

Co et al., Properties and pharmacokinetics of two humanized antibodies specific for L-selectin. Immunotechnology. Mar. 1999;4(3-4):253-66.

Colman, Effects of amino acid sequence changes on antibody-antigen interactions. Res Immunol. Jan. 1994;145(1):33-6.

Diacovo et al., Interactions of human alpha/beta and gamma/delta T lymphocyte subsets in shear flow with E-selectin and P-selectin. J Exp Med. Mar. 1996;183:1193-1203.

Dimitroff et al., Glycosylation-dependent inhibition of cutaneous lymphocyte-associated antigen expression: Implications in modulating lymphocyte migration to skin. Blood. Jan. 15, 2003;101(2):602-10.

Ellison et al., Linkage and sequence homology of two human immunoglobulin gamma heavy chain constant region genes. Proc Natl Acad Sci U S A. Mar. 1982;79(6):1984-8.

Ellison et al., The nucleotide sequence of a human immunoglobulin C gamma 1 gene. Nucleic Acids Res. Jul. 10, 1982;10(13):4071-9.

Evangelista et al., Platelet/polymorphonuclear leukocyte interaction: P-selectin triggers protein-tyrosine phosphorylation-dependent CD11b/CD18 adhesion: Role of PSGL-1 as a signaling molecule. Blood. Feb. 1, 1999;93(3):876-85.

Faraday et al., Leukocytes can enhance platelet-mediated aggregation and thromboxane release via interaction of P-selectin glycoprotein ligand 1 with P-selectin. Anesthesiology. Jan. 2001;94(1):145-51.

Frenette, et al., P-selectin glycoprotein ligand 1 (PSGL-1) is expressed on platelets and can mediate platelet-endothelial interactions in vivo. J Exp Med. Apr. 17, 2000;191(8):1413-22.

Fuhlbrigge et al., Cutaneous lymphocyte antigen is a specialized form of PSGL-I expressed on skin-homing T cells. Nature. Oct. 1997;389:978-81.

He et al., Humanization and pharmacokinetics of a monoclonal antibody with specificity for both E- and P-selectin. J Immunol. Jan. 15, 1998;160(2):1029-35.

Herron et al., Intracellular parasitism by the human granulocytic ehrlichiosis bacterium through the P-selectin ligand, PSGL-1. Science. Jun. 2, 2000;288(5471):1653-6.

Hieter et al., Cloned human and mouse kappa immunoglobulin constant and J region genes conserve homology in functional segments. Cell. Nov. 1980;22(1 Pt 1):197-207.

Hirata et al., P-selectin glycoprotein ligand 1 (PSGL-1) is a physiological ligand for E-selectin in mediating t helper 1 lymphocyte migration. J Exp Med. Dec. 4, 2000;192(11):1669-75.

Hirose et al., A functional epitope on P-selectin that supports binding of P-selectin to P-selectin glycoprotein ligand-1 but not to sialyl Lewis X oligosaccharides. Internatl Immunol. Jan. 26, 1998;10(5):639-49.

Huang et al., A novel apoptosis-inducing anti-PSGL-1 antibody for T cell-mediated diseases. Eur J Immunol. 2005;35(7):2239-49.

Hwang et al., GlyCAM-1, a physiologic ligand for L-selectin, activates beta 2 integrins on naive peripheral lymphocytes. J Exp Med. Oct. 1, 1996;184(4):1343-8.

Igarashi et al., Telomerase activity is induced in human peripheral B lymphocytes by the stimulation to antigen receptor. Blood. 1997;89(4):1299-1307.

Kaytes et al., P-selectin mediates 1-37 adhesion of the human melanoma cell line NKI-4: Identification of glycoprotein ligands. Biochemistry. Jul. 21, 1998;37(29):10514-21.

Kieffer et al., Neutrophilis, monocytes, and dendritic cells express the same specialized form of PSGL-1 as do skin-homing memory T cells: Cutaneous lymphocyte antigen. Biochem Biophys Res Comm. Jul. 20, 2001;285(3):577-87.

Laszik et al., P-selectin glycoprotein ligand-1 is broadly expressed in cells of myeloid, lymphoid, and dendritic lineage and in some nonhematopoietic cells. Blood. Oct. 15, 1996;88(8):3010-21.

Levesque et al., PSGL-1-mediated adhesion of human hematopoietic progenitors to P-selectin results in suppression of hematopoiesis. Immunity. Sep. 1999;11:369-78.

Li et al., Visualization of P-selectin glycoprotein ligand-1 as a highly extended molecule and mapping of protein epitopes for monoclonal antibodies. J Biol Chem. 1996;271(11):6342-8.

Moore et al., P-selectin glycoprotein ligand-1 mediates rolling of human neutrophils on P-selectin. J Cell Biol. 1995;128(4):661-71.

Queen et al., A humanized antibody that binds to the interleukin 2 receptor. Proc Natl Acad Sci U S A. Dec. 1989;86(24):10029-33.

Rudikoff et al., Single amino acid substitution altering antigen-binding specificity. Proc Natl Acad Sci USA. 1982;79:1979-83.

Sako et al., Expression cloning of a functional glycoprotein ligand for P-selectin. Cell. Dec. 17, 1993;75(6):1179-86.

Shan et al., Apoptosis of malignant human B cells by ligation of CD20 with monoclonal antibodies. Blood. 1998;91(5):1644-52.

Snapp et al., A novel P-selectin glycoprotein ligand-1 monoclonal antibody recognizes an epitope within the tyrosine sulfate motif of human PSGL-1 and blocks recognition of both P-and L-selectin. Blood. Jan. 1, 1998;91(1):154-64.

Stockmeyer et al., Polymorphonuclear granulocytes induce antibody-dependent apoptosis in human breast cancer cells. J Immunol. 2003;171:5124-9.

Strausberg et al., Generation and initial analysis of more than 15,000 full-length human and mouse cDNA sequences. Proc Natl Acad Sci U S A. Dec. 24, 2002;99(26):16899-903. Epub Dec. 11, 2002.

Thatte et al., Binding of function-blocking mAbs to mouse and human P-selectin glycoprotein ligand-1 peptides with and without tyrosine sulfation, J Leukoc Biol. Sep. 2002;72(3):470-7.

Trembleau et al., Pancreas-infiltrating Th1 cells and diabetes develop in IL-12 deficient nonobese diabetic mice. J Immunol. 1999;163:2960-8.

Vachino et al., P-selectin glycoprotein ligand-1 is the major counter-receptor for P-selectin on stimulated T cells and is widely distributed in non-functional form on many lymphocytic cells. J Biol Chem. Sep. 15, 1995;270(37):21966-74.

Veldman et al., Genomic organization and chromosomal localization of the gene encoding human P-selectin glycoprotein ligand. J Biol Chem. Jul. 7, 1995;270(27):16470-5.

Wing et al., Mechanism of first-dose cytokine-release syndrome by CAMPATH 1-H: Involvement of CD16 (FcγR111) and CD11a/CD18 (LFA-1) on NK cells. J Clin Invest 1996;98(12):2819-26.

Woltmann et al., Interleukin-13 induces PSGL-1/P-selectin-dependent adhesion of eosinophils, but not neutrophils, to human umbilical vein endothelial cells under flow. Blood. May 15, 2000;95(10): 3146-52.

Wu et al., Role of P-selectin and anti-P-selectin monoclonal antibody in apoptosis during hepatic/renal ischemia reperfusion injury. World J Gastroentero. 2000;6(2):244-7.

Yago et al., IL-12 Promotes the adhesion of NK cells to endothelial selectins under flow conditions. J Immunol. 1998;161:1140-45.

Yang et al., Targeted gene disruption demonstrates that P-selectin glycoprotein ligand 1 (PSGL-1) is required for P-selectin-mediated but not E-selectin-mediated neutrophil rolling and migration. J Exp Med. Dec. 20, 1999;190(12):1769-82.

Yang et al., The biology of P-selectin glycoprotein ligand-1: its role as a selectin counterreceptor in leukocyte-endothelial and leukocyte-platelet interaction. Thrombosis Haemostasis. 1999;81(1):1-7.

Moiseenko, Monoclonal antibodies in treatment of cancer tumors. Practical Oncology. 2003; 4(3):148-156.

Singer et al., The genetic molecules. Genes and Genomes. vol. 1; 1998. Chapter 1: 63, 66.

* cited by examiner

SEQUENCE LISTING

```
<160> NUMBER OF SEQ ID NOS: 100

<210> SEQ ID NO 1
<211> LENGTH: 16
<212> TYPE: PRT
<213> ORGANISM: Mus musculus

<400> SEQUENCE: 1

Arg Ser Ser Gln Ser Ile Val His Asn Asp Gly Asn Thr Tyr Phe Glu
1               5                   10                  15

<210> SEQ ID NO 2
<211> LENGTH: 7
<212> TYPE: PRT
<213> ORGANISM: Mus musculus

<400> SEQUENCE: 2

Lys Val Ser Asn Arg Phe Ser
1               5

<210> SEQ ID NO 3
<211> LENGTH: 9
<212> TYPE: PRT
<213> ORGANISM: Mus musculus

<400> SEQUENCE: 3

Phe Gln Gly Ser Tyr Val Pro Leu Thr
1               5
```

<210> SEQ ID NO 4
<211> LENGTH: 5
<212> TYPE: PRT
<213> ORGANISM: Mus musculus

<400> SEQUENCE: 4

Ser Phe Gly Met His
 1               5

<210> SEQ ID NO 5
<211> LENGTH: 17
<212> TYPE: PRT
<213> ORGANISM: Mus musculus

<400> SEQUENCE: 5

Tyr Ile Asn Gly Gly Ser Ser Thr Ile Phe Tyr Ala Asn Ala Val Lys
 1               5                  10                  15

Gly

<210> SEQ ID NO 6
<211> LENGTH: 11
<212> TYPE: PRT
<213> ORGANISM: Mus musculus

<400> SEQUENCE: 6

Tyr Ala Ser Tyr Gly Gly Gly Ala Met Asp Tyr
 1               5                  10

<210> SEQ ID NO 7
<211> LENGTH: 12
<212> TYPE: PRT
<213> ORGANISM: Mus musculus

<400> SEQUENCE: 7

Arg Ala Ser Ser Thr Val Asn Ser Thr Tyr Leu His
 1               5                  10

<210> SEQ ID NO 8
<211> LENGTH: 7
<212> TYPE: PRT
<213> ORGANISM: Mus musculus

<400> SEQUENCE: 8

Gly Ser Ser Asn Leu Ala Ser
 1               5

<210> SEQ ID NO 9
<211> LENGTH: 9
<212> TYPE: PRT
<213> ORGANISM: Mus musculus

<400> SEQUENCE: 9

Gln Gln Tyr Ser Gly Tyr Pro Leu Thr
 1               5

<210> SEQ ID NO 10
<211> LENGTH: 5
<212> TYPE: PRT
<213> ORGANISM: Mus musculus

<400> SEQUENCE: 10

Ala Tyr Tyr Ile His
 1               5

```
<210> SEQ ID NO 11
<211> LENGTH: 16
<212> TYPE: PRT
<213> ORGANISM: Mus musculus

<400> SEQUENCE: 11

Val Asn Pro Asn Thr Gly Gly Thr Ser Tyr Asn Pro Lys Phe Lys Gly
1               5                   10                  15

<210> SEQ ID NO 12
<211> LENGTH: 10
<212> TYPE: PRT
<213> ORGANISM: Mus musculus

<400> SEQUENCE: 12

Ser Gly Ser Pro Tyr Tyr Arg Tyr Asp Asp
1               5                   10

<210> SEQ ID NO 13
<211> LENGTH: 16
<212> TYPE: PRT
<213> ORGANISM: Mus musculus

<400> SEQUENCE: 13

Arg Ser Ser Gln Ser Ile Val Asn Ser Asn Gly Asn Thr Tyr Leu Glu
1               5                   10                  15

<210> SEQ ID NO 14
<211> LENGTH: 7
<212> TYPE: PRT
<213> ORGANISM: Mus musculus

<400> SEQUENCE: 14

Lys Val Ser Asn Arg Phe Ser
1               5

<210> SEQ ID NO 15
<211> LENGTH: 9
<212> TYPE: PRT
<213> ORGANISM: Mus musculus

<400> SEQUENCE: 15

Phe Gln Gly Ser His Val Pro Trp Thr
1               5

<210> SEQ ID NO 16
<211> LENGTH: 16
<212> TYPE: PRT
<213> ORGANISM: Mus musculus

<400> SEQUENCE: 16

Thr Asn Ala Met Asn Trp Val Arg Gln Ala Pro Gly Lys Gly Leu Glu
1               5                   10                  15

<210> SEQ ID NO 17
<211> LENGTH: 9
<212> TYPE: PRT
<213> ORGANISM: Mus musculus

<400> SEQUENCE: 17

Thr Tyr Tyr Ala Asp Ser Val Lys Asp
1               5

<210> SEQ ID NO 18
<211> LENGTH: 9
<212> TYPE: PRT
```

```
<213> ORGANISM: Mus musculus

<400> SEQUENCE: 18

Gly Gly Ser Tyr Trp Tyr Phe Asp Val
1               5

<210> SEQ ID NO 19
<211> LENGTH: 131
<212> TYPE: PRT
<213> ORGANISM: Mus musculus

<400> SEQUENCE: 19

Met Lys Leu Pro Val Arg Leu Leu Val Leu Met Phe Trp Ile Pro Ala
1               5                   10                  15

Ser Ser Ser Asp Ile Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val His Asn Asp Gly Asn Thr Tyr Phe Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr His Phe Thr
                85                  90                  95

Leu Asn Ile Ser Arg Val Glu Ala Glu Asp Leu Gly Ile Tyr Tyr Cys
            100                 105                 110

Phe Gln Gly Ser Tyr Val Pro Leu Thr Phe Gly Ala Gly Thr Lys Leu
        115                 120                 125

Glu Leu Lys
    130

<210> SEQ ID NO 20
<211> LENGTH: 139
<212> TYPE: PRT
<213> ORGANISM: Mus musculus

<400> SEQUENCE: 20

Met Asp Ser Arg Leu Asn Leu Val Phe Leu Val Leu Ile Leu Lys Gly
1               5                   10                  15

Val Gln Cys Asp Val Gln Leu Val Glu Ser Gly Gly Gly Leu Val Gln
            20                  25                  30

Pro Gly Gly Ser Arg Lys Leu Ser Cys Ala Ala Ser Gly Phe Thr Phe
        35                  40                  45

Ser Ser Phe Gly Met His Trp Val Arg Gln Ala Pro Glu Lys Gly Leu
    50                  55                  60

Glu Trp Val Ala Tyr Ile Asn Gly Gly Ser Ser Thr Ile Phe Tyr Ala
65                  70                  75                  80

Asn Ala Val Lys Gly Arg Phe Thr Ile Ser Arg Asp Asn Pro Lys Asn
                85                  90                  95

Thr Leu Phe Leu Gln Met Thr Ile Leu Arg Ser Glu Asp Thr Ala Ile
            100                 105                 110

Tyr Tyr Cys Gly Arg Tyr Ala Ser Tyr Gly Gly Ala Met Asp Tyr
        115                 120                 125

Trp Gly Gln Gly Thr Ser Val Thr Val Ser Ser
    130                 135

<210> SEQ ID NO 21
<211> LENGTH: 130
```

```
<212> TYPE: PRT
<213> ORGANISM: Mus musculus

<400> SEQUENCE: 21

Met Asp Phe Leu Val Gln Ile Phe Ser Phe Leu Leu Ile Ser Ala Ser
 1               5                   10                  15

Val Ala Met Ser Arg Gly Glu Asn Val Leu Thr Gln Ser Pro Ala Ile
            20                  25                  30

Met Ser Ala Ser Pro Gly Glu Lys Val Thr Met Thr Cys Arg Ala Ser
        35                  40                  45

Ser Thr Val Asn Ser Thr Tyr Leu His Trp Phe Gln Gln Lys Ser Gly
    50                  55                  60

Ala Ser Pro Lys Leu Trp Ile Tyr Gly Ser Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Val Glu Ala Glu Asp Ala Ala Thr Tyr Tyr Cys Gln
            100                 105                 110

Gln Tyr Ser Gly Tyr Pro Leu Thr Phe Gly Ala Gly Thr Thr Leu Glu
        115                 120                 125

Leu Lys
    130

<210> SEQ ID NO 22
<211> LENGTH: 138
<212> TYPE: PRT
<213> ORGANISM: Mus musculus

<400> SEQUENCE: 22

Met Glu Trp Ser Trp Val Phe Leu Phe Leu Leu Ser Val Thr Thr Gly
 1               5                   10                  15

Val His Ser Glu Val Gln Leu Gln Gln Ser Gly Pro Asp Leu Val Lys
            20                  25                  30

Pro Gly Ala Leu Val Lys Ile Ser Cys Lys Ala Ser Gly Tyr Ser Phe
        35                  40                  45

Thr Ala Tyr Tyr Ile His Trp Val Lys Gln Ser His Gly Lys Ser Leu
    50                  55                  60

Glu Trp Ile Gly Arg Val Asn Pro Asn Thr Gly Gly Thr Ser Tyr Asn
65                  70                  75                  80

Pro Lys Phe Lys Gly Lys Ala Ile Leu Asn Val Asp Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Ala Arg Ser Gly Ser Pro Tyr Tyr Arg Tyr Asp Asp Trp
        115                 120                 125

Gly Gln Gly Thr Thr Leu Thr Val Ser Ser
    130                 135

<210> SEQ ID NO 23
<211> LENGTH: 131
<212> TYPE: PRT
<213> ORGANISM: Mus musculus

<400> SEQUENCE: 23

Met Lys Leu Pro Val Arg Leu Leu Val Leu Met Phe Trp Ile Pro Ala
 1               5                   10                  15

Ser Ser Ser Asp Val Leu Met Thr Gln Thr Pro Leu Ser Leu Pro Val
            20                  25                  30
```

Ser Leu Gly Asp Gln Ala Ser Ile Ser Cys Arg Ser Ser Gln Ser Ile
            35                  40                  45

Val Asn Ser Asn Gly Asn Thr Tyr Leu Glu Trp Tyr Leu Gln Lys Pro
 50                  55                  60

Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
               100                 105                 110

Phe Gln Gly Ser His Val Pro Trp Thr Phe Gly Gly Gly Thr Lys Leu
               115                 120                 125

Glu Ile Lys
       130

<210> SEQ ID NO 24
<211> LENGTH: 139
<212> TYPE: PRT
<213> ORGANISM: Mus musculus

<400> SEQUENCE: 24

Met Leu Leu Gly Leu Lys Trp Val Phe Phe Val Val Phe Tyr Gln Gly
 1               5                  10                  15

Val His Cys Glu Val Gln Leu Val Glu Thr Gly Gly Gly Leu Val Gln
                20                  25                  30

Pro Lys Gly Ser Leu Lys Leu Ser Cys Ala Ala Ser Gly Phe Thr Phe
            35                  40                  45

Asn Thr Asn Ala Met Asn Trp Val Arg Gln Ala Pro Gly Lys Gly Leu
 50                  55                  60

Glu Trp Val Ala Arg Ile Arg Ser Lys Ser Asn Asn Tyr Ala Thr Tyr
 65                  70                  75                  80

Tyr Ala Asp Ser Val Lys Asp Arg Phe Thr Ile Ser Arg Asp Asp Thr
                85                  90                  95

Gln Ser Met Ile Tyr Leu Gln Met Asn Asn Leu Lys Thr Glu Asp Thr
               100                 105                 110

Gly Met Tyr Tyr Cys Val Arg Gly Gly Ser Tyr Trp Tyr Phe Asp Val
               115                 120                 125

Trp Gly Ala Gly Thr Thr Val Thr Val Ser Ser
           130                 135

<210> SEQ ID NO 25
<211> LENGTH: 112
<212> TYPE: PRT
<213> ORGANISM: Artificial Sequence
<220> FEATURE:
<223> OTHER INFORMATION: Synthetically generated peptide

<400> SEQUENCE: 25

Asp Ile Gln Met Thr Gln Ser Pro Ser Ser Leu Ser Ala Ser Val Gly
 1               5                  10                  15

Asp Arg Val Thr Ile Thr Cys Arg Ser Ser Gln Ser Ile Val His Asn
                20                  25                  30

Asp Gly Asn Thr Tyr Phe Glu Trp Tyr Gln Gln Lys Pro Gly Lys Ala
            35                  40                  45

Pro Lys Leu Leu Ile Tyr Lys Val Ser Asn Arg Phe Ser Gly Val Pro
 50                  55                  60

Ser Arg Phe Ser Gly Ser Gly Ser Gly Thr His Phe Thr Leu Thr Ile

```
                      65                  70                  75                  80
Ser Ser Leu Gln Pro Glu Asp Phe Ala Thr Tyr Tyr Cys Phe Gln Gly
                85                  90                  95

Ser Tyr Val Pro Leu Thr Phe Gly Gln Gly Thr Lys Val Glu Ile Lys
              100                 105                 110

<210> SEQ ID NO 26
<211> LENGTH: 120
<212> TYPE: PRT
<213> ORGANISM: Artificial Sequence
<220> FEATURE:
<223> OTHER INFORMATION: Synthetically generated peptide

<400> SEQUENCE: 26

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Phe
                20                  25                  30

Gly Met His Trp Val Arg Gln Ala Pro Gly Lys Gly Leu Glu Trp Val
              35                  40                  45

Ala Tyr Ile Asn Gly Gly Ser Ser Thr Ile Phe Tyr Ala Asn Ala Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Tyr Ala Ser Tyr Gly Gly Ala Met Asp Tyr Trp Gly Gln
              100                 105                 110

Gly Thr Leu Val Thr Val Ser Ser
              115                 120

<210> SEQ ID NO 27
<211> LENGTH: 393
<212> TYPE: DNA
<213> ORGANISM: Mus musculus
<220> FEATURE:
<221> NAME/KEY: CDS
<222> LOCATION: (1)...(393)

<400> SEQUENCE: 27 atg aag ttg cct gtt agg ctg ttg gtg ctg atg ttc tgg att cct gct       48
Met Lys Leu Pro Val Arg Leu Leu Val Leu Met Phe Trp Ile Pro Ala
  1               5                  10                  15 tcc agc agt gat att ttg atg acc caa act cca ctg tcc ctg cct gtc       96
Ser Ser Ser Asp Ile Leu Met Thr Gln Thr Pro Leu Ser Leu Pro Val
                20                  25                  30 agt ctt gga gat caa gcc tca ata tct tgc aga tct agt cag agc att      144
Ser Leu Gly Asp Gln Ala Ser Ile Ser Cys Arg Ser Ser Gln Ser Ile
              35                  40                  45 gta cat aat gat gga aac acc tat ttt gaa tgg tac ctg cag aaa cca      192
Val His Asn Asp Gly Asn Thr Tyr Phe Glu Trp Tyr Leu Gln Lys Pro
 50                  55                  60 ggc cag tct cca aaa ctc ctg atc tac aaa gtt tcc aat cga ttt tct      240
Gly Gln Ser Pro Lys Leu Leu Ile Tyr Lys Val Ser Asn Arg Phe Ser
 65                  70                  75                  80 ggg gtc cca gac agg ttc agt ggc agt gga tca ggg aca cat ttc aca      288
Gly Val Pro Asp Arg Phe Ser Gly Ser Gly Ser Gly Thr His Phe Thr
                85                  90                  95 ctc aac atc agc aga gtg gag gct gag gat ctg gga att tat tac tgc      336
Leu Asn Ile Ser Arg Val Glu Ala Glu Asp Leu Gly Ile Tyr Tyr Cys
              100                 105                 110
```

```
ttt caa ggt tca tat gtt cct ctc acg ttc ggt gct ggg acc aag ctg      384
Phe Gln Gly Ser Tyr Val Pro Leu Thr Phe Gly Ala Gly Thr Lys Leu
        115                 120                 125 gag ctg aaa                                                          393
Glu Leu Lys
    130

<210> SEQ ID NO 28
<211> LENGTH: 417
<212> TYPE: DNA
<213> ORGANISM: Mus musculus
<220> FEATURE:
<221> NAME/KEY: CDS
<222> LOCATION: (1)...(417)

<400> SEQUENCE: 28 atg gac tcc agg ctc aat tta gtt ttc ctt gtc ctt att tta aaa ggt      48
Met Asp Ser Arg Leu Asn Leu Val Phe Leu Val Leu Ile Leu Lys Gly
1               5                   10                  15 gtc cag tgt gat gtg cag ctg gtg gag tct ggg gga ggc tta gtg cag      96
Val Gln Cys Asp Val Gln Leu Val Glu Ser Gly Gly Gly Leu Val Gln
            20                  25                  30 cct gga ggg tcc cgg aaa ctc tcc tgt gca gcc tct gga ttc act ttc      144
Pro Gly Gly Ser Arg Lys Leu Ser Cys Ala Ala Ser Gly Phe Thr Phe
        35                  40                  45 agt agc ttt gga atg cac tgg gtt cgt cag gct cca gag aag ggg ctg      192
Ser Ser Phe Gly Met His Trp Val Arg Gln Ala Pro Glu Lys Gly Leu
    50                  55                  60 gag tgg gtc gca tac att aat ggt ggc agt agt acc atc ttc tat gca      240
Glu Trp Val Ala Tyr Ile Asn Gly Gly Ser Ser Thr Ile Phe Tyr Ala
65                  70                  75                  80 aac gca gtg aag ggc cga ttc acc atc tcc aga gac aat ccc aag aat      288
Asn Ala Val Lys Gly Arg Phe Thr Ile Ser Arg Asp Asn Pro Lys Asn
                85                  90                  95 acc ctg ttc ctg caa atg acc att cta agg tct gag gac acg gcc att      336
Thr Leu Phe Leu Gln Met Thr Ile Leu Arg Ser Glu Asp Thr Ala Ile
            100                 105                 110 tat tac tgt gga agg tat gct agt tac gga ggg ggt gct atg gac tat      384
Tyr Tyr Cys Gly Arg Tyr Ala Ser Tyr Gly Gly Gly Ala Met Asp Tyr
        115                 120                 125 tgg ggt caa gga acc tca gtc acc gtc tcc tca                          417
Trp Gly Gln Gly Thr Ser Val Thr Val Ser Ser
    130                 135

<210> SEQ ID NO 29
<211> LENGTH: 390
<212> TYPE: DNA
<213> ORGANISM: Mus musculus
<220> FEATURE:
<221> NAME/KEY: CDS
<222> LOCATION: (1)...(390)

<400> SEQUENCE: 29 atg gat ttt ctg gtg cag att ttc agc ttc ttg cta atc agt gcc tca      48
Met Asp Phe Leu Val Gln Ile Phe Ser Phe Leu Leu Ile Ser Ala Ser
1               5                   10                  15 gtt gca atg tcc aga gga gaa aat gtg ctc acc cag tct cca gca atc      96
Val Ala Met Ser Arg Gly Glu Asn Val Leu Thr Gln Ser Pro Ala Ile
            20                  25                  30 atg tct gca tct cca ggg gaa aag gtc acc atg acc tgc agg gcc agc      144
Met Ser Ala Ser Pro Gly Glu Lys Val Thr Met Thr Cys Arg Ala Ser
        35                  40                  45 tca act gta aat tcc act tac ttg cac tgg ttc cag cag aag tca ggt      192
```

```
                                                                         -continued Ser Thr Val Asn Ser Thr Tyr Leu His Trp Phe Gln Gln Lys Ser Gly
         50                  55                  60 gcc tcc ccc aaa ctc tgg att tat ggc tca tcc aac ttg gct tct gga       240
Ala Ser Pro Lys Leu Trp Ile Tyr Gly Ser Ser Asn Leu Ala Ser Gly
 65                  70                  75                  80 gtc cct gct cgc ttc agt ggc agt ggg tct ggg acc tct tac tct ctc       288
Val Pro Ala Arg Phe Ser Gly Ser Gly Ser Gly Thr Ser Tyr Ser Leu
                 85                  90                  95 aca atc agc agt gtg gag gct gaa gat gct gcc act tat tac tgc cag       336
Thr Ile Ser Ser Val Glu Ala Glu Asp Ala Ala Thr Tyr Tyr Cys Gln
            100                 105                 110 cag tac agt ggt tac cca ctc acg ttc ggt gct ggg acc acg ctg gag       384
Gln Tyr Ser Gly Tyr Pro Leu Thr Phe Gly Ala Gly Thr Thr Leu Glu
        115                 120                 125 ctg aaa                                                                390
Leu Lys
    130

<210> SEQ ID NO 30
<211> LENGTH: 414
<212> TYPE: DNA
<213> ORGANISM: Mus musculus
<220> FEATURE:
<221> NAME/KEY: CDS
<222> LOCATION: (1)...(414)

<400> SEQUENCE: 30 atg gaa tgg agc tgg gtc ttt ctc ttc ctc ctg tca gtc act aca ggt        48
Met Glu Trp Ser Trp Val Phe Leu Phe Leu Leu Ser Val Thr Thr Gly
  1               5                  10                  15 gtc cac tct gag gtc cag ctg cag cag tct gga cct gac ctg gtg aag        96
Val His Ser Glu Val Gln Leu Gln Gln Ser Gly Pro Asp Leu Val Lys
             20                  25                  30 cct ggg gct tta gtg aag ata tcc tgc aag gct tct ggt tac tca ttc       144
Pro Gly Ala Leu Val Lys Ile Ser Cys Lys Ala Ser Gly Tyr Ser Phe
         35                  40                  45 act gcc tac tac att cac tgg gtg aag cag agc cat gga aag agc ctt       192
Thr Ala Tyr Tyr Ile His Trp Val Lys Gln Ser His Gly Lys Ser Leu
     50                  55                  60 gag tgg att gga cgt gtt aat cct aat act ggt ggt act agc tac aac       240
Glu Trp Ile Gly Arg Val Asn Pro Asn Thr Gly Gly Thr Ser Tyr Asn
 65                  70                  75                  80 ccg aag ttc aag ggc aag gcc ata tta aat gta gat aag tca tcc agc       288
Pro Lys Phe Lys Gly Lys Ala Ile Leu Asn Val Asp Lys Ser Ser Ser
                 85                  90                  95 aca gcc tac atg gag ctc cgc agc ctg aca tct gag gac tct gcg gtc       336
Thr Ala Tyr Met Glu Leu Arg Ser Leu Thr Ser Glu Asp Ser Ala Val
            100                 105                 110 tat tac tgt gca aga tcg gga tcc ccc tac tat agg tac gac gac tgg       384
Tyr Tyr Cys Ala Arg Ser Gly Ser Pro Tyr Tyr Arg Tyr Asp Asp Trp
        115                 120                 125 ggc caa ggc acc act ctc aca gtc tcc tca                               414
Gly Gln Gly Thr Thr Leu Thr Val Ser Ser
    130                 135

<210> SEQ ID NO 31
<211> LENGTH: 393
<212> TYPE: DNA
<213> ORGANISM: Mus musculus
<220> FEATURE:
<221> NAME/KEY: CDS
<222> LOCATION: (1)...(393)

<400> SEQUENCE: 31
```

```
atg aag ttg cct gtt agg ctg ttg gtg ctg atg ttc tgg att cct gct    48
Met Lys Leu Pro Val Arg Leu Leu Val Leu Met Phe Trp Ile Pro Ala
 1               5                  10                  15 tcc agc agt gat gtt ttg atg acc caa act cca ctc tcc ctg cct gtc    96
Ser Ser Ser Asp Val Leu Met Thr Gln Thr Pro Leu Ser Leu Pro Val
             20                  25                  30 agt ctt gga gat caa gcc tcc atc tct tgc aga tct agt cag agc att   144
Ser Leu Gly Asp Gln Ala Ser Ile Ser Cys Arg Ser Ser Gln Ser Ile
         35                  40                  45 gta aat agt aat gga aac acc tat tta gaa tgg tac ctg cag aaa cca   192
Val Asn Ser Asn Gly Asn Thr Tyr Leu Glu Trp Tyr Leu Gln Lys Pro
     50                  55                  60 ggc cag tct cca aag ctc ctg atc tac aaa gtt tcc aac cga ttt tct   240
Gly Gln Ser Pro Lys Leu Leu Ile Tyr Lys Val Ser Asn Arg Phe Ser
 65                  70                  75                  80 ggg gtc cca gac agg ttc agt ggc agt gga tca ggg aca gat ttc aca   288
Gly Val Pro Asp Arg Phe Ser Gly Ser Gly Ser Gly Thr Asp Phe Thr
                 85                  90                  95 ctc aag atc agc aga gtg gag gct gag gat ctg gga gtt tat tac tgc   336
Leu Lys Ile Ser Arg Val Glu Ala Glu Asp Leu Gly Val Tyr Tyr Cys
             100                 105                 110 ttt caa ggt tca cat gtt ccg tgg acg ttc ggt gga ggc acc aag ctg   384
Phe Gln Gly Ser His Val Pro Trp Thr Phe Gly Gly Gly Thr Lys Leu
         115                 120                 125 gaa atc aaa                                                       393
Glu Ile Lys
    130

<210> SEQ ID NO 32
<211> LENGTH: 417
<212> TYPE: DNA
<213> ORGANISM: Mus musculus
<220> FEATURE:
<221> NAME/KEY: CDS
<222> LOCATION: (1)...(417)

<400> SEQUENCE: 32 atg ctg ttg ggg ctg aag tgg gtt ttc ttt gtt gtt ttt tat caa ggt    48
Met Leu Leu Gly Leu Lys Trp Val Phe Phe Val Val Phe Tyr Gln Gly
 1               5                  10                  15 gtg cat tgt gag gtg cag ctt gtt gag act gga gga gga ttg gtg cag    96
Val His Cys Glu Val Gln Leu Val Glu Thr Gly Gly Gly Leu Val Gln
             20                  25                  30 cct aaa ggg tca ttg aaa ctc tca tgt gca gcc tct gga ttc acc ttc   144
Pro Lys Gly Ser Leu Lys Leu Ser Cys Ala Ala Ser Gly Phe Thr Phe
         35                  40                  45 aat acc aat gcc atg aac tgg gtc cgc cag gct cca gga aag ggt ttg   192
Asn Thr Asn Ala Met Asn Trp Val Arg Gln Ala Pro Gly Lys Gly Leu
     50                  55                  60 gaa tgg gtt gct cgc ata aga agt aaa agt aat aat tat gca aca tat   240
Glu Trp Val Ala Arg Ile Arg Ser Lys Ser Asn Asn Tyr Ala Thr Tyr
 65                  70                  75                  80 tat gcc gat tca gtg aaa gac agg ttc acc atc tcc aga gat gat aca   288
Tyr Ala Asp Ser Val Lys Asp Arg Phe Thr Ile Ser Arg Asp Asp Thr
                 85                  90                  95 caa agc atg atc tat ctg caa atg aac aac ttg aaa act gag gac aca   336
Gln Ser Met Ile Tyr Leu Gln Met Asn Asn Leu Lys Thr Glu Asp Thr
             100                 105                 110 ggc atg tat tac tgt gtg aga ggg gga agc tac tgg tac ttc gat gtc   384
Gly Met Tyr Tyr Cys Val Arg Gly Gly Ser Tyr Trp Tyr Phe Asp Val
         115                 120                 125
```

```
tgg ggc gca ggg acc acg gtc acc gtc tcc tca                          417
Trp Gly Ala Gly Thr Thr Val Thr Val Ser Ser
130                 135
```

<210> SEQ ID NO 33
<211> LENGTH: 111
<212> TYPE: PRT
<213> ORGANISM: Mus musculus

<400> SEQUENCE: 33

```
Asp Ile Val Leu Thr Gln Ser Pro Ala Ser Leu Ser Val Ser Leu Gly
1               5                   10                  15

Glu Arg Ala Ser Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Trp Thr Phe Gly Gly Gly Thr Lys Leu Glu Ile Lys
            100                 105                 110
```

<210> SEQ ID NO 34
<211> LENGTH: 112
<212> TYPE: PRT
<213> ORGANISM: Mus musculus

<400> SEQUENCE: 34

```
Asp Ile Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Asn
            20                  25                  30

Asp Gly Asn Thr Tyr Phe Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr His Phe Thr Leu Asn Ile
65                  70                  75                  80

Ser Arg Val Glu Ala Glu Asp Leu Gly Ile Tyr Tyr Cys Phe Gln Gly
                85                  90                  95

Ser Tyr Val Pro Leu Thr Phe Gly Ala Gly Thr Lys Leu Glu Leu Lys
            100                 105                 110
```

<210> SEQ ID NO 35
<211> LENGTH: 116
<212> TYPE: PRT
<213> ORGANISM: Mus musculus

<400> SEQUENCE: 35

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Thr Tyr
            20                  25                  30

Ala Met Ser Trp Val Arg Gln Thr Pro Glu Lys Arg Leu Glu Trp Val
        35                  40                  45

Ala Ser Ile Ser Thr Gly Gly Ser Thr Tyr Tyr Pro Asp Ser Val Lys
```

```
                50                  55                  60
Gly Arg Phe Thr Ile Ser Arg Asp Asn Ala Arg Asn Ile Leu Tyr Leu
 65                  70                  75                  80

Gln Met Ser Ser Leu Arg Ser Glu Asp Thr Ala Met Tyr Tyr Cys Ala
                 85                  90                  95

Arg Asp Tyr Asp Gly Tyr Phe Asp Tyr Trp Gly Gln Gly Thr Thr Leu
                100                 105                 110

Thr Val Ser Ser
            115

<210> SEQ ID NO 36
<211> LENGTH: 120
<212> TYPE: PRT
<213> ORGANISM: Mus musculus

<400> SEQUENCE: 36

Asp Val Gln Leu Val Glu Ser Gly Gly Leu Val Gln Pro Gly Gly
  1               5                  10                  15

Ser Arg Lys Leu Ser Cys Ala Ala Ser Gly Phe Thr Phe Ser Ser Phe
                 20                  25                  30

Gly Met His Trp Val Arg Gln Ala Pro Glu Lys Gly Leu Glu Trp Val
             35                  40                  45

Ala Tyr Ile Asn Gly Gly Ser Ser Thr Ile Phe Tyr Ala Asn Ala Val
 50                  55                  60

Lys Gly Arg Phe Thr Ile Ser Arg Asp Asn Pro Lys Asn Thr Leu Phe
 65                  70                  75                  80

Leu Gln Met Thr Ile Leu Arg Ser Glu Asp Thr Ala Ile Tyr Tyr Cys
                 85                  90                  95

Gly Arg Tyr Ala Ser Tyr Gly Gly Ala Met Asp Tyr Trp Gly Gln
                100                 105                 110

Gly Thr Ser Val Thr Val Ser Ser
            115                 120

<210> SEQ ID NO 37
<211> LENGTH: 111
<212> TYPE: PRT
<213> ORGANISM: Homo sapiens

<400> SEQUENCE: 37

Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Ser Val Asp Tyr Asp
                 20                  25                  30

Gly Asp Ser Tyr Met Asn Trp Tyr Gln Gln Lys Pro Gly Lys Ala Pro
             35                  40                  45

Lys Leu Leu Ile Tyr Ala Ala Ser Asn Leu Glu Ser Gly Ile Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Asn
                 85                  90                  95

Glu Asp Pro Trp Thr Phe Gly Gln Gly Thr Lys Val Glu Ile Lys
                100                 105                 110

<210> SEQ ID NO 38
<211> LENGTH: 116
<212> TYPE: PRT
<213> ORGANISM: Homo sapiens
```

<400> SEQUENCE: 38

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Thr | Tyr |
|---|---|---|---|---|---|---|---|---|---|---|---|---|---|---|---|
| | | | 20 | | | | | 25 | | | | | 30 | | |

| Ala | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | | 35 | | | | | 40 | | | | | 45 | | |

| Ala | Ser | Ile | Ser | Thr | Gly | Gly | Ser | Thr | Tyr | Tyr | Pro | Asp | Ser | Val | Lys |
|---|---|---|---|---|---|---|---|---|---|---|---|---|---|---|---|
| | 50 | | | | | 55 | | | | | 60 | | | | |

| Gly | Arg | Phe | Thr | Ile | Ser | Arg | Asp | Asn | Ala | Lys | Asn | Thr | Leu | Tyr | Leu |
|---|---|---|---|---|---|---|---|---|---|---|---|---|---|---|---|
| 65 | | | | | 70 | | | | | 75 | | | | | 80 |

| Gln | Met | Asn | Ser | Leu | Arg | Ala | Glu | Asp | Thr | Ala | Val | Tyr | Tyr | Cys | Ala |
|---|---|---|---|---|---|---|---|---|---|---|---|---|---|---|---|
| | | | | 85 | | | | | 90 | | | | | 95 | |

| Arg | Asp | Tyr | Asp | Gly | Tyr | Phe | Asp | Tyr | Trp | Gly | Gln | Gly | Thr | Leu | Val |
|---|---|---|---|---|---|---|---|---|---|---|---|---|---|---|---|
| | | | 100 | | | | | 105 | | | | | 110 | | |

| Thr | Val | Ser | Ser |
|---|---|---|---|
| | | | 115 |

<210> SEQ ID NO 39
<211> LENGTH: 36
<212> TYPE: DNA
<213> ORGANISM: Artificial Sequence
<220> FEATURE:
<223> OTHER INFORMATION: Primer

<400> SEQUENCE: 39
cccgggacca tatgcaggcc accgaatatg agtacc       36

<210> SEQ ID NO 40
<211> LENGTH: 37
<212> TYPE: DNA
<213> ORGANISM: Artificial Sequence
<220> FEATURE:
<223> OTHER INFORMATION: Primer

<400> SEQUENCE: 40
tatgagcata tggattatga tttcctgcca gaaacgg      37

<210> SEQ ID NO 41
<211> LENGTH: 41
<212> TYPE: DNA
<213> ORGANISM: Artificial Sequence
<220> FEATURE:
<223> OTHER INFORMATION: Primer

<400> SEQUENCE: 41
aaacggagca tatggaaatg ctgaggaaca gcactgacac c    41

<210> SEQ ID NO 42
<211> LENGTH: 39
<212> TYPE: DNA
<213> ORGANISM: Artificial Sequence
<220> FEATURE:
<223> OTHER INFORMATION: Primer

<400> SEQUENCE: 42
aacccctcat atgaccactg tggagcctgc tgcaaggcg     39

<210> SEQ ID NO 43
<211> LENGTH: 39
<212> TYPE: DNA
<213> ORGANISM: Artificial Sequence

```
<220> FEATURE:
<223> OTHER INFORMATION: Primer

<400> SEQUENCE: 43
gtggtcagat cttccatagc tgctgaatcc gtggacagg                              39

<210> SEQ ID NO 44
<211> LENGTH: 37
<212> TYPE: DNA
<213> ORGANISM: Artificial Sequence
<220> FEATURE:
<223> OTHER INFORMATION: Primer

<400> SEQUENCE: 44
gttcctcaga tcttctggag gctccgtttc tggcagg                               37

<210> SEQ ID NO 45
<211> LENGTH: 37
<212> TYPE: DNA
<213> ORGANISM: Artificial Sequence
<220> FEATURE:
<223> OTHER INFORMATION: Primer

<400> SEQUENCE: 45
aggcccaaga tctggagtgg tgtcagtgct gttcctc                               37

<210> SEQ ID NO 46
<211> LENGTH: 35
<212> TYPE: DNA
<213> ORGANISM: Artificial Sequence
<220> FEATURE:
<223> OTHER INFORMATION: Primer

<400> SEQUENCE: 46
ggctccagat ctgtagactc aggggttcca ggccc                                 35

<210> SEQ ID NO 47
<211> LENGTH: 38
<212> TYPE: DNA
<213> ORGANISM: Artificial Sequence
<220> FEATURE:
<223> OTHER INFORMATION: Primer

<400> SEQUENCE: 47
gtggtcagat ctgtgactgc ccctcctgca tccaggcc                              38

<210> SEQ ID NO 48
<211> LENGTH: 37
<212> TYPE: DNA
<213> ORGANISM: Artificial Sequence
<220> FEATURE:
<223> OTHER INFORMATION: Primer

<400> SEQUENCE: 48
gccagcagat cttgcttcac agagatgtgg tctgggg                               37

<210> SEQ ID NO 49
<211> LENGTH: 34
<212> TYPE: DNA
<213> ORGANISM: Artificial Sequence
<220> FEATURE:
<223> OTHER INFORMATION: Primer

<400> SEQUENCE: 49
cgcggatcca tgcctctgca actcctcctg ttgc                                  34
```

-continued

```
<210> SEQ ID NO 50
<211> LENGTH: 35
<212> TYPE: DNA
<213> ORGANISM: Artificial Sequence
<220> FEATURE:
<223> OTHER INFORMATION: Primer

<400> SEQUENCE: 50
gccagcctcg agcttcacag agatgtggtc tgggg                              35

<210> SEQ ID NO 51
<211> LENGTH: 40
<212> TYPE: DNA
<213> ORGANISM: Artificial Sequence
<220> FEATURE:
<223> OTHER INFORMATION: Primer

<400> SEQUENCE: 51
ggtctgctcg agcatagctg ctgaatccgt ggacaggttc                         40

<210> SEQ ID NO 52
<211> LENGTH: 30
<212> TYPE: DNA
<213> ORGANISM: Artificial Sequence
<220> FEATURE:
<223> OTHER INFORMATION: Primer

<400> SEQUENCE: 52
agacaggcca ccgaagggaa cctgtccacg                                    30

<210> SEQ ID NO 53
<211> LENGTH: 30
<212> TYPE: DNA
<213> ORGANISM: Artificial Sequence
<220> FEATURE:
<223> OTHER INFORMATION: Primer

<400> SEQUENCE: 53
cgtggacagg ttcccttcgg tggcctgtct                                    30

<210> SEQ ID NO 54
<211> LENGTH: 27
<212> TYPE: DNA
<213> ORGANISM: Artificial Sequence
<220> FEATURE:
<223> OTHER INFORMATION: Primer

<400> SEQUENCE: 54
ccgctcgagc gccaagatta ggatggc                                       27

<210> SEQ ID NO 55
<211> LENGTH: 27
<212> TYPE: DNA
<213> ORGANISM: Artificial Sequence
<220> FEATURE:
<223> OTHER INFORMATION: Primer

<400> SEQUENCE: 55
cgggatccac tcaaaccaca gccatgg                                       27

<210> SEQ ID NO 56
<211> LENGTH: 27
<212> TYPE: DNA
<213> ORGANISM: Artificial Sequence
<220> FEATURE:
<223> OTHER INFORMATION: Primer

<400> SEQUENCE: 56
```

```
ccgctcgagt ggtagtaggt tccatgg                                          27

<210> SEQ ID NO 57
<211> LENGTH: 26
<212> TYPE: DNA
<213> ORGANISM: Artificial Sequence
<220> FEATURE:
<223> OTHER INFORMATION: Primer

<400> SEQUENCE: 57
cgggatcaac tcaacccaca ggcctg                                           26

<210> SEQ ID NO 58
<211> LENGTH: 28
<212> TYPE: DNA
<213> ORGANISM: Artificial Sequence
<220> FEATURE:
<223> OTHER INFORMATION: Primer

<400> SEQUENCE: 58
ctgtgcctcg agggctgtgg tttgagtg                                         28

<210> SEQ ID NO 59
<211> LENGTH: 30
<212> TYPE: DNA
<213> ORGANISM: Artificial Sequence
<220> FEATURE:
<223> OTHER INFORMATION: Primer

<400> SEQUENCE: 59
cgggatccat ggagatacag accactcaac                                       30

<210> SEQ ID NO 60
<211> LENGTH: 28
<212> TYPE: DNA
<213> ORGANISM: Artificial Sequence
<220> FEATURE:
<223> OTHER INFORMATION: Primer

<400> SEQUENCE: 60
cgggatccga tgcaggaggg gcagtcac                                         28

<210> SEQ ID NO 61
<211> LENGTH: 27
<212> TYPE: DNA
<213> ORGANISM: Artificial Sequence
<220> FEATURE:
<223> OTHER INFORMATION: Primer

<400> SEQUENCE: 61
ggccgtcact cgagttgtct gtgcctc                                          27

<210> SEQ ID NO 62
<211> LENGTH: 43
<212> TYPE: DNA
<213> ORGANISM: Artificial Sequence
<220> FEATURE:
<223> OTHER INFORMATION: Primer

<400> SEQUENCE: 62
tatggattca gcagctatgg agatacagac cactcaacca gca                        43

<210> SEQ ID NO 63
<211> LENGTH: 45
<212> TYPE: DNA
<213> ORGANISM: Artificial Sequence
```

```
<220> FEATURE:
<223> OTHER INFORMATION: Primer

<400> SEQUENCE: 63
gatctgctgg ttgagtggtc tgtatctcca tagctgctga atcca        45

<210> SEQ ID NO 64
<211> LENGTH: 43
<212> TYPE: DNA
<213> ORGANISM: Artificial Sequence
<220> FEATURE:
<223> OTHER INFORMATION: Primer

<400> SEQUENCE: 64
tatggattca gcagctatgc ggatacagac cactcaacca gca          43

<210> SEQ ID NO 65
<211> LENGTH: 45
<212> TYPE: DNA
<213> ORGANISM: Artificial Sequence
<220> FEATURE:
<223> OTHER INFORMATION: Primer

<400> SEQUENCE: 65
gatctgctgg ttgagtggtc tgtatccgca tagctgctga atcca        45

<210> SEQ ID NO 66
<211> LENGTH: 31
<212> TYPE: DNA
<213> ORGANISM: Artificial Sequence
<220> FEATURE:
<223> OTHER INFORMATION: Primer

<400> SEQUENCE: 66
ctagtctaga tgacccaaac tccactctcc c                       31

<210> SEQ ID NO 67
<211> LENGTH: 49
<212> TYPE: DNA
<213> ORGANISM: Artificial Sequence
<220> FEATURE:
<223> OTHER INFORMATION: Primer

<400> SEQUENCE: 67
ctagtctaga attaggaaag tgcacttagc atcagcccgt ttgatttcc    49

<210> SEQ ID NO 68
<211> LENGTH: 33
<212> TYPE: DNA
<213> ORGANISM: Artificial Sequence
<220> FEATURE:
<223> OTHER INFORMATION: Primer

<400> SEQUENCE: 68
taacattcta gatgctgttg gggctgaagt ggg                     33

<210> SEQ ID NO 69
<211> LENGTH: 49
<212> TYPE: DNA
<213> ORGANISM: Artificial Sequence
<220> FEATURE:
<223> OTHER INFORMATION: Primer

<400> SEQUENCE: 69
ggatagtcta gaggttgtga ggactcacct gaggagacgg tgaccgtgg    49
```

```
<210> SEQ ID NO 70
<211> LENGTH: 37
<212> TYPE: DNA
<213> ORGANISM: Artificial Sequence
<220> FEATURE:
<223> OTHER INFORMATION: Primer

<400> SEQUENCE: 70
ctagtctaga tggagacaga cacactcctg ttatggg                         37

<210> SEQ ID NO 71
<211> LENGTH: 49
<212> TYPE: DNA
<213> ORGANISM: Artificial Sequence
<220> FEATURE:
<223> OTHER INFORMATION: Primer

<400> SEQUENCE: 71
ctagtctaga attaggaaag tgcacttttt ccagcttggt cccccctcc            49

<210> SEQ ID NO 72
<211> LENGTH: 37
<212> TYPE: DNA
<213> ORGANISM: Artificial Sequence
<220> FEATURE:
<223> OTHER INFORMATION: Primer

<400> SEQUENCE: 72
ctagtctaga tggactccag gctcaattta gttttcc                         37

<210> SEQ ID NO 73
<211> LENGTH: 51
<212> TYPE: DNA
<213> ORGANISM: Artificial Sequence
<220> FEATURE:
<223> OTHER INFORMATION: Primer

<400> SEQUENCE: 73
ctagtctaga ggttgtgagg actcacctga ggagacggtg actgaggttc c         51

<210> SEQ ID NO 74
<211> LENGTH: 36
<212> TYPE: DNA
<213> ORGANISM: Artificial Sequence
<220> FEATURE:
<223> OTHER INFORMATION: Primer

<400> SEQUENCE: 74
ctagtctaga tggattttct ggtgcagatt ttcagc                          36

<210> SEQ ID NO 75
<211> LENGTH: 49
<212> TYPE: DNA
<213> ORGANISM: Artificial Sequence
<220> FEATURE:
<223> OTHER INFORMATION: Primer

<400> SEQUENCE: 75
ctagtctaga attaggaaag tgcacttagc atcagcccgt ttcagctcc            49

<210> SEQ ID NO 76
<211> LENGTH: 33
<212> TYPE: DNA
<213> ORGANISM: Artificial Sequence
<220> FEATURE:
<223> OTHER INFORMATION: Primer

<400> SEQUENCE: 76
```

```
ctagtctaga tggaatggag ctgggtcttt ctc                                    33

<210> SEQ ID NO 77
<211> LENGTH: 51
<212> TYPE: DNA
<213> ORGANISM: Artificial Sequence
<220> FEATURE:
<223> OTHER INFORMATION: Primer

<400> SEQUENCE: 77
ctagtctaga ggttgtgagg actcaccagc ttccagtgga tagactgatg g                51

<210> SEQ ID NO 78
<211> LENGTH: 65
<212> TYPE: DNA
<213> ORGANISM: Artificial Sequence
<220> FEATURE:
<223> OTHER INFORMATION: Primer

<400> SEQUENCE: 78
tctatctaga tgaacttcgg gtccagcttg attttccttg tccttgtttt aaaaggtgtc       60
cagtg                                                                  65

<210> SEQ ID NO 79
<211> LENGTH: 69
<212> TYPE: DNA
<213> ORGANISM: Artificial Sequence
<220> FEATURE:
<223> OTHER INFORMATION: Primer

<400> SEQUENCE: 79
ccttgtttta aaaggtgtcc agtgtgaagt gcaactggtg gagtctgggg gaggcttagt       60
gcagcctgg                                                              69

<210> SEQ ID NO 80
<211> LENGTH: 65
<212> TYPE: DNA
<213> ORGANISM: Artificial Sequence
<220> FEATURE:
<223> OTHER INFORMATION: Primer

<400> SEQUENCE: 80
ctgaaagtga atccagaggc tgcacaggag agtctcaagc ttcctccagg ctgcactaag       60
cctcc                                                                  65

<210> SEQ ID NO 81
<211> LENGTH: 69
<212> TYPE: DNA
<213> ORGANISM: Artificial Sequence
<220> FEATURE:
<223> OTHER INFORMATION: Primer

<400> SEQUENCE: 81
gcctctggat tcactttcag tagctttgga atgcactggg ttcgccaggc tccagggaag       60
ggactcgag                                                              69

<210> SEQ ID NO 82
<211> LENGTH: 66
<212> TYPE: DNA
<213> ORGANISM: Artificial Sequence
<220> FEATURE:
<223> OTHER INFORMATION: Primer

<400> SEQUENCE: 82
```

```
gcatagaaga tggtactact gccaccatta atgtatgcga cccactcgag tcccttccct    60
ggagcc                                                               66

<210> SEQ ID NO 83
<211> LENGTH: 62
<212> TYPE: DNA
<213> ORGANISM: Artificial Sequence
<220> FEATURE:
<223> OTHER INFORMATION: Primer

<400> SEQUENCE: 83
gtagtaccat cttctatgca aacgcagtga agggccgatt caccatctcc agagataatg    60
cc                                                                   62

<210> SEQ ID NO 84
<211> LENGTH: 63
<212> TYPE: DNA
<213> ORGANISM: Artificial Sequence
<220> FEATURE:
<223> OTHER INFORMATION: Primer

<400> SEQUENCE: 84
cctcagccct cagagaattc atttgcaggt acagggtgtt cttggcatta tctctggaga    60
tgg                                                                  63

<210> SEQ ID NO 85
<211> LENGTH: 63
<212> TYPE: DNA
<213> ORGANISM: Artificial Sequence
<220> FEATURE:
<223> OTHER INFORMATION: Primer

<400> SEQUENCE: 85
gaattctctg agggctgagg acacggccgt gtattactgt gcaagatatg ctagttacgg    60
agg                                                                  63

<210> SEQ ID NO 86
<211> LENGTH: 60
<212> TYPE: DNA
<213> ORGANISM: Artificial Sequence
<220> FEATURE:
<223> OTHER INFORMATION: Primer

<400> SEQUENCE: 86
ctgtgaccag ggtgccttgg ccccaatagt ccatagcacc ccctccgtaa ctagcatatc    60

<210> SEQ ID NO 87
<211> LENGTH: 57
<212> TYPE: DNA
<213> ORGANISM: Artificial Sequence
<220> FEATURE:
<223> OTHER INFORMATION: Primer

<400> SEQUENCE: 87
accctctaga ggttgtgagg actcacctga ggagactgtg accagggtgc cttggcc       57

<210> SEQ ID NO 88
<211> LENGTH: 60
<212> TYPE: DNA
<213> ORGANISM: Artificial Sequence
<220> FEATURE:
<223> OTHER INFORMATION: Primer

<400> SEQUENCE: 88
```

```
tctatctaga tggagacaga cacaatcctg ctatgggtgc tgctgctctg ggttccaggc    60
```

<210> SEQ ID NO 89
<211> LENGTH: 61
<212> TYPE: DNA
<213> ORGANISM: Artificial Sequence
<220> FEATURE:
<223> OTHER INFORMATION: Primer

<400> SEQUENCE: 89

```
gctgctctgg gttccaggct ccactggtga cattcagatg acccaatctc cgagctcttt    60
g                                                                   61
```

<210> SEQ ID NO 90
<211> LENGTH: 60
<212> TYPE: DNA
<213> ORGANISM: Artificial Sequence
<220> FEATURE:
<223> OTHER INFORMATION: Primer

<400> SEQUENCE: 90

```
gatctgcagg tgatagtgac cctatcccct acagacgcag acaaagagct cggagattgg    60
```

<210> SEQ ID NO 91
<211> LENGTH: 63
<212> TYPE: DNA
<213> ORGANISM: Artificial Sequence
<220> FEATURE:
<223> OTHER INFORMATION: Primer

<400> SEQUENCE: 91

```
cactatcacc tgcagatcta gtcagagcat tgtacataat gatggaaaca cctattttga    60
atg                                                                 63
```

<210> SEQ ID NO 92
<211> LENGTH: 59
<212> TYPE: DNA
<213> ORGANISM: Artificial Sequence
<220> FEATURE:
<223> OTHER INFORMATION: Primer

<400> SEQUENCE: 92

```
gatgagaagc ttgggtgcct ttcctggttt ctgttggtac cattcaaaat aggtgtttc     59
```

<210> SEQ ID NO 93
<211> LENGTH: 66
<212> TYPE: DNA
<213> ORGANISM: Artificial Sequence
<220> FEATURE:
<223> OTHER INFORMATION: Primer

<400> SEQUENCE: 93

```
gcacccaagc ttctcatcta taaagtttcc aatcgatttt ctggtgtccc atccaggttt    60
agtggc                                                              66
```

<210> SEQ ID NO 94
<211> LENGTH: 61
<212> TYPE: DNA
<213> ORGANISM: Artificial Sequence
<220> FEATURE:
<223> OTHER INFORMATION: Primer

<400> SEQUENCE: 94

```
gcagagaaga gatggtgagg gtgaagtgtg tcccagaccc actgccacta aacctggatg    60
``` g                                                              61

<210> SEQ ID NO 95
<211> LENGTH: 55
<212> TYPE: DNA
<213> ORGANISM: Artificial Sequence
<220> FEATURE:
<223> OTHER INFORMATION: Primer

<400> SEQUENCE: 95
ctcaccatct cttctctgca gccggaggat ttcgcaacct attactgttt tcaag      55

<210> SEQ ID NO 96
<211> LENGTH: 57
<212> TYPE: DNA
<213> ORGANISM: Artificial Sequence
<220> FEATURE:
<223> OTHER INFORMATION: Primer

<400> SEQUENCE: 96
ccttggtgcc ttgaccgaac gtgagaggaa catatgaacc ttgaaaacag taatagg    57

<210> SEQ ID NO 97
<211> LENGTH: 58
<212> TYPE: DNA
<213> ORGANISM: Artificial Sequence
<220> FEATURE:
<223> OTHER INFORMATION: Primer

<400> SEQUENCE: 97
accctctaga attaggaaag tgcacttacg tttgatttcc accttggtgc cttgaccg   58

<210> SEQ ID NO 98
<211> LENGTH: 30
<212> TYPE: DNA
<213> ORGANISM: Artificial Sequence
<220> FEATURE:
<223> OTHER INFORMATION: Primer

<400> SEQUENCE: 98
tatatctaga attcccccccc ccccccccc                                  30

<210> SEQ ID NO 99
<211> LENGTH: 46
<212> TYPE: DNA
<213> ORGANISM: Artificial Sequence
<220> FEATURE:
<223> OTHER INFORMATION: Primer

<400> SEQUENCE: 99
tatagagctc aagcttggat ggtgggaaga tggatacagt tggtgc                46

<210> SEQ ID NO 100
<211> LENGTH: 50
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 30
<223> OTHER INFORMATION: n = c, a or t
<220> FEATURE:
<221> NAME/KEY: misc_feature
<222> LOCATION: 38
<223> OTHER INFORMATION: n = c or g
<220> FEATURE:
<221> NAME/KEY: misc_feature

```
<222> LOCATION: 42
<223> OTHER INFORMATION: n = c or t

<400> SEQUENCE: 100
tatagagctc aagcttccag tggatagacn gatggggntg tngttttggc          50
```

ANTI-PSGL-1 ANTIBODIES

RELATED APPLICATIONS

This application is a continuation of U.S. application Ser. No. 12/399,516, filed Mar. 6, 2009, now abandoned, which is a continuation of U.S. patent application Ser. No. 11/125,837, filed May 10, 2005 now U.S. Pat. No. 7,604,800, which claims priority to U.S. Provisional Application No. 60/569,892, filed May 10, 2004, the contents of all of which are incorporated by reference in their entirety.

BACKGROUND

Overly aggressive T cells often lead to unwanted immune responses, which, in turn, cause various disorders, e.g., autoimmune diseases, transplant rejection, allergic diseases, and T cell-derived cancers. Therefore, control of the aggressive T cells is critical in treating such disorders. The activity of these cells can be contained by immunosuppression or by induction of immunological tolerance. An alternative solution is induction of apoptosis, which is believed to be involved in removing unwanted cells, including overly aggressive T cells. See, e.g., Kabelitz et al. (1993) *Immunol Today* 14, 338-340; and Raff (1992) *Nature* 356, 397-399.

SUMMARY

This invention relates to antibodies and their derivatives that induce apoptosis upon binding to P-Selectin Glycoprotein Ligand-1 (PSGL-1) on activated T cells.

In one aspect, the invention features an immunoglobulin chain having three sequences that (i) contain, respectively, RSSQSIVHNDGNTYFE, KVSNRFS, and FQGSYVPLT (SEQ ID NOs: 1-3); (ii) contain, respectively, SFGMH, YINGGSSTIFYANAVKG, and YASYGGGAMDY (SEQ ID NOs: 4-6); (iii) contain, respectively, RASSTVNSTYLH, GSSNLAS, and QQYSGYPLT (SEQ ID NOs: 7-9); (iv) contain, respectively, AYYIH, VNPNTGGTSYNPKFKG, and SGSPYYRYDD (SEQ ID NOs: 10-12); (v) contain, respectively, RSSQSIVNSNGNTYLE, KVSNRFS, and FQGSHVPWT (SEQ ID NOs: 13-15); or (vi) contain, respectively, TNAMNWVRQAPGKGLE, TYYADSVKD, and GGSYWYFDV (SEQ ID NOs: 16-18).

Each of the just-described six sets of sequences corresponds to the three light or heavy chain complementarity determining regions (CDRs) of an antibody that binds to PSGL-1, such as those of three mouse 15A7, 43B6, and 9F9 antibodies described in the examples below. Shown below are the light chains and heavy chain variable (V) regions of these three antibodies (SEQ ID NOs: 19-26, the CDRs are underlined and highlighted):

Nucleic acid SEQ ID NO: 19 and amino acid SEQ ID NO: 27 (Mouse 15A7 light chain V region):

```
  1 ATGAAGTTGCCTGTTAGGCTGTTGGTGCTGATGTTCTGGATTCCTGCTTCCAGCAGTGAT
  1 M  K  L  P  V  R  L  L  V  L  M  F  W  I  P  A  S  S  S  D

61 ATTTTGATGACCCAAACTCCACTGTCCCTGCCTGTCAGTCTTGGAGATCAAGCCTCAATA
 21 I  L  M  T  Q  T  P  L  S  L  P  V  S  L  G  D  Q  A  S  I

121 TCTTGCAGATCTAGTCAGAGCATTGTACATAATGATGGAAACACCTATTTTGAATGGTAC
 41 S  C  R  S  S  Q  S  I  V  H  N  D  G  N  T  Y  F  E  W  Y

181 CTGCAGAAACCAGGCCAGTCTCCAAAACTCCTGATCTACAAAGTTTCCAATCGATTTTCT
 61 L  Q  K  P  G  Q  S  P  K  L  L  I  Y  K  V  S  N  R  F  S

241 GGGGTCCCAGACAGGTTCAGTGGCAGTGGATCAGGGACACATTTCACACTCAACATCAGC
 81 G  V  P  D  R  F  S  G  S  G  S  G  T  H  F  T  L  N  I  S

301 AGAGTGGAGGCTGAGGATCTGGGAATTTATTACTGCTTTCAAGGTTCATATGTTCCTCTC
101 R  V  E  A  E  D  L  G  I  Y  Y  C  F  Q  G  S  Y  V  P  L

361 ACGTTCGGTGCTGGGACCAAGCTGGAGCTGAAA
121 T  F  G  A  G  T  K  L  E  L  K
```

Nucleic acid SEQ ID NO: 20 and amino acid SEQ ID NO: 28 (Mouse 15A7 heavy chain V region):

```
  1 ATGGACTCCAGGCTCAATTTAGTTTTCCTTGTCCTTATTTTAAAAGGTGTCCAGTGTGAT
  1 M  D  S  R  L  N  L  V  F  L  V  L  I  L  K  G  V  Q  C  D

61 GTGCAGCTGGTGGAGTCTGGGGGAGGCTTAGTGCAGCCTGGAGGGTCCCGGAAACTCTCC
 21 V  Q  L  V  E  S  G  G  G  L  V  Q  P  G  G  S  R  K  L  S

121 TGTGCAGCCTCTGGATTCACTTTCAGTAGCTTTGGAATGCACTGGGTTCGTCAGGCTCCA
 41 C  A  A  S  G  F  T  F  S  S  F  G  M  H  W  V  R  Q  A  P

181 GAGAAGGGGCTGGAGTGGGTCGCATACATTAATGGTGGCAGTAGTACCATCTTCTATGCA
 61 E  K  G  L  E  W  V  A  Y  I  N  G  G  S  S  T  I  F  Y  A

241 AACGCAGTGAAGGGCCGATTCACCATCTCCAGAGACAATCCCAAGAATACCCTGTTCCTG
 81 N  A  V  K  G  R  F  T  I  S  R  D  N  P  K  N  T  L  F  L

301 CAAATGACCATTCTAAGGTCTGAGGACACGGCCATTTATTACTGTGGAAGGTATGCTAGT
101 Q  M  T  I  L  R  S  E  D  T  A  I  Y  Y  C  G  R  Y  A  S

361 TACGGAGGGGGTGCTATGGACTATTGGGGTCAAGGAACCTCAGTCACCGTCTCCTCA
121 Y  G  G  G  A  M  D  Y  W  G  Q  G  T  S  V  T  V  S  S
```

Nucleic acid SEQ ID NO: 21 and amino acid SEQ ID NO: 29
(Mouse 43B6 light chain V region):

```
  1 ATGGATTTTCTGGTGCAGATTTTCAGCTTCTTGCTAATCAGTGCCTCAGTTGCAATGTCC
  1  M  D  F  L  V  Q  I  F  S  F  L  L  I  S  A  S  V  A  M  S
 61 AGAGGAGAAAATGTGCTCACCCAGTCTCCAGCAATCATGTCTGCATCTCCAGGGGAAAAG
 21  R  G  E  N  V  L  T  Q  S  P  A  I  M  S  A  S  P  G  E  K
121 GTCACCATGACCTGCAGGGCCAGCTCAACTGTAAATTCCACTTACTTGCACTGGTTCCAG
 41  V  T  M  T  C  R  A  S  S  T  V  N  A  T  Y  L  H  W  F  Q
181 CAGAAGTCAGGTGCCTCCCCCAAACTCTGGATTTATGGCTCATCCAACTTGGCTTCTGGA
 61  Q  K  S  G  A  S  P  K  L  W  I  Y  G  S  S  N  L  A  S  G
241 GTCCCTGCTCGCTTCAGTGGCAGTGGGTCTGGGACCTCTTACTCTCTCACAATCAGCAGT
 81  V  P  A  R  F  S  G  S  G  S  G  T  S  Y  S  L  T  I  S  S
301 GTGGAGGCTGAAGATGCTGCCACTTATTACTGCCAGCAGTACAGTGGTTACCCACTCACG
101  V  E  A  E  D  A  A  T  Y  Y  C  Q  Q  Y  S  G  Y  P  L  T
361 TTCGGTGCTGGGACCACGCTGGAGCTGAAA
121  F  G  A  G  T  T  L  E  L  K
```

Nucleic acid SEQ ID NO: 22 and amino acid SEQ ID NO: 30
(Mouse 43B6 heavy chain V region):

```
  1 ATGGAATGGAGCTGGGTCTTTCTCTTCCTCCTGTCAGTCACTACAGGTGTCCACTCTGAG
  1  M  E  W  S  W  V  F  L  F  L  L  S  V  T  T  G  V  H  S  E
 61 GTCCAGCTGCAGCAGTCTGGACCTGACCTGGTGAAGCCTGGGGCTTTAGTGAAGATATCC
 21  V  Q  L  Q  Q  S  G  P  D  L  V  K  P  G  A  L  V  K  I  S
121 TGCAAGGCTTCTGGTTACTCATTCACTGCCTACTACATTCACTGGGTGAAGCAGAGCCAT
 41  C  K  A  S  G  Y  S  F  T  A  Y  Y  I  H  W  V  K  Q  S  H
181 GGAAAGAGCCTTGAGTGGATTGGACGTGTTAATCCTAATACTGGTGGTACTAGCTACAAC
 61  G  K  S  L  E  W  I  G  R  V  N  P  N  T  G  G  T  S  Y  N
241 CCGAAGTTCAAGGGCAAGGCCATATTAAATGTAGATAAGTCATCCAGCACAGCCTATATG
 81  P  K  F  K  G  K  A  I  L  N  V  D  K  S  S  S  T  A  Y  M
301 GAGCTCCGCAGCCTGACATCTGAGGACTCTGCGGTCTATTACTGTGCAAGATCGGGATCC
101  E  L  R  S  L  T  S  E  D  S  A  V  Y  Y  C  A  R  S  G  S
361 CCCTACTATAGGTACGACGACTGGGGCCAAGGCACCACTCTCACAGTCTCCTCA
121  P  Y  Y  R  Y  D  D  W  G  Q  G  T  T  L  T  V  S  S
```

Nucleic acid SEQ ID NO: 23 and amino acid SEQ ID NO: 31
(Mouse 9F9 light chain V region):

```
  1 ATGAAGTTGCCTGTTAGGCTGTTGGTGCTGATGTTCTGGATTCCTGCTTCCAGCAGTGAT
  1  M  K  L  P  V  R  L  L  V  L  M  F  W  I  P  A  S  S  S  D
 61 GTTTTGATGACCCAAACTCCACTCTCCCTGCCTGTCAGTCTTGGAGATCAAGCCTCCATC
 21  V  L  M  T  Q  T  P  L  S  L  P  V  S  L  G  D  Q  A  S  I
121 TCTTGCAGATCTAGTCAGAGCATTGTAAATAGTAATGGAAACACCTATTTAGAATGGTAC
 41  S  C  R  S  S  Q  S  I  V  N  S  N  G  N  T  Y  L  E  W  Y
181 CTGCAGAAACCAGGCCAGTCTCCAAAGCTCCTGATCTACAAAGTTTCCAACCGATTTTCT
 61  L  Q  K  P  G  Q  S  P  K  L  L  I  Y  K  V  S  N  R  F  S
241 GGGGTCCCAGACAGGTTCAGTGGCAGTGGATCAGGGACAGATTTCACACTCAAGATCAGC
 81  G  V  P  D  R  F  S  G  S  G  S  G  T  D  F  T  L  K  I  S
301 AGAGTGGAGGCTGAGGATCTGGGAGTTTATTACTGCTTTCAAGGTTCACATGTTCCGTGG
101  R  V  E  A  E  D  L  G  V  Y  Y  C  F  Q  G  S  H  V  P  W
361 ACGTTCGGTGGAGGCACCAAGCTGGAAATCAAA
121  T  F  G  G  G  T  K  L  E  I  K
```

Nucleic acid SEQ ID NO: 24 and amino acid SEQ ID NO: 32
(Mouse 9F9 heavy chain V region):

```
  1 ATGCTGTTGGGGCTGAAGTGGGTTTTCTTTGTTGTTTTTTATCAAGGTGTGCATTGTGAG
  1  M  L  L  G  L  K  W  V  F  F  V  V  F  Y  Q  G  V  H  C  E
 61 GTGCAGCTTGTTGAGACTGGTGGAGGATTGGTGCAGCCTAAAGGGTCATTGAAACTCTCA
 21  V  Q  L  V  E  T  G  G  G  L  V  Q  P  K  G  S  L  K  L  S
121 TGTGCAGCCTCTGGATTCACCTTCAATACCAATGCCATGAACTGGGTCCGCCAGGCTCCA
 41  C  A  A  S  G  F  T  F  N  T  N  A  M  N  W  V  R  Q  A  P
```

-continued

```
181 GGAAAGGGTTTGGAATGGGTTGCTCGCATAAGAAGTAAAAGTAATAATTATGCAACATAT
 61  G  K  G  L  E  W  V  A  R  I  R  S  K  S  N  N  Y  A  I  Y
241 TATGCCGATTCAGTGAAAGACAGGTTCACCATCTCCAGAGATGATACACAAAGCATGATC
 81  Y  A  D  S  V  K  D  R  F  T  I  S  R  D  D  T  Q  S  M  I
301 TATCTGCAAATGAACAACTTGAAAACTGAGGACACAGGCATGTATTACTGTGTGAGAGGG
101  Y  L  Q  M  N  N  L  K  T  E  D  T  G  M  Y  Y  C  V  R  G
361 GGAAGCTACTGGTACTTCGATGTCTGGGGCGCAGGGACCACGGTCACCGTCTCCTCA
121  G  S  Y  W  Y  F  D  V  W  G  A  G  T  T  V  T  V  S  S
```

As an antibody's antigen-binding specificity is determined by its light and heavy chain CDRs, the above-described CDRs can be used to generate antibody derivatives that retain the antigen-binding specificity. Examples of antibody derivatives include chimeric antibodies, humanized antibodies, and their functional equivalents. Shown below are the light chain V region (SEQ ID NO: 25) and heavy chain V region (SEQ ID NO: 26) of a humanized 15A7 antibody, which include SEQ ID NOs: 1-3 and SEQ ID NOs: 4-6, respectively:

SEQ ID NO: 25 (humanized 15A7 light chain V region):

DIQMTQSPSSLSASVGDRVTITCRSSQSIVHSDGNTYFEWYQQKPGKAPKLLIYKVSNRFSGVPSRFSGSG

SGTHFTLTISSLQPEDFATYYCFQGSYVPLTFGQGTKVEIK

SEQ ID NO: 26 (humanized 15A7 heavy chain V region):

EVQLVESGGGLVQPGGSLRLSCAASGFTFSSFKGMHWVRQAPGKGLEWVAYINSGSSTIFYANAVKGRFTIS

RDNAKNTLYLQMNSLRAEDTAVYYCARYASYGGAMDYWGQGTLVTVSS

This invention also features an isolated nucleic acid having a sequence that encodes one of the above-described immunoglobulin chains. The term "antibody" or "immunoglobulin chain" refers to an isolated polypeptide, i.e., a polypeptide that has been substantially separated from other proteins, lipids, and nucleic acids with which it is naturally associated. The polypeptide can constitute at least 50, 70, or 95% by dry weight of the purified preparation. An "isolated nucleic acid" refers to a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. The nucleic acid of this invention can be used to express a polypeptide of this invention. For this purpose, one can operatively link the nucleic acid to suitable regulatory sequences to generate an expression vector.

A vector refers to a nucleic acid molecule capable of transporting another nucleic acid to which it has been linked, and also capable of autonomous replication or integration into a host DNA. Examples include a plasmid, cosmid, and viral vector. A vector of this invention includes a nucleic acid in a form suitable for expression of the nucleic acid in a host cell.

Preferably, the vector includes one or more regulatory sequences operatively linked to the nucleic acid sequence to be expressed. Examples of a regulatory sequence include promoters, enhancers, and other expression control elements (e.g., polyadenylation signals). Regulatory sequences also include those that direct constitutive expression of a nucleotide sequence, as well as tissue-specific regulatory and/or inducible sequences. The design of such an expression vector is based on considerations including the choice of the host cell to be transformed and the desired expression level. An expression vector can be introduced into host cells to produce a polypeptide of this invention. This invention also includes a host cell that contains the above-described nucleic acid. A host cell refers to a cell containing an exogenous coding sequence or non-coding sequence. An exogenous sequence can be introduced into a cell by calcium phosphate transfection, DEAE-Dextran mediated transfection, or electroporation. Suitable host cells include bacterial cells (e.g., *E. coli, Bacillus subtilis,* and *Salmonella typhimurium*), yeast cells (e.g., *Saccharomyces cerevisiae* and *Schizosaccharomyces pombe*), plant cells (e.g., *Nicotiana tabacum* and *Gossypium hirsutum*), and mammalian cells (e.g., murine hybridoma cells, CHO cells, and 3T3 fibroblasts).

To produce an immunoglobulin chain of this invention, one can place a host cell in a culture under conditions permitting expression of a polypeptide encoded by a nucleic acid described above, and isolate the polypeptide from the culture. Alternatively, a nucleic acid of this invention can be transcribed and translated in vitro, for example, using T7 promoter regulatory sequences and T7 polymerase.

Within the scope of this invention is an antibody. It is formed by a first immunoglobulin chain and a second immunoglobulin chain, which contain, respectively, the light chain CDRs and heavy chain CDRs of the mouse 15A7, 43B6, or 9F9 antibody mentioned above. Preferably, this antibody is formed by the light and heavy chains of 15A7.

Also within the scope of this invention is another antibody that (i) binds specifically to P-Selectin Glycoprotein Ligand 1 without interfering with binding between P-Selectin Glycoprotein Ligand 1 and P-Selectin and, (ii), upon binding to P-Selectin Glycoprotein Ligand 1 on an activated T cell, induces the death of the T cell. In one embodiment, this antibody binds specifically to human P-Selectin Glycoprotein Ligand 1.

Further within the scope of this invention is still another antibody that binds specifically to amino acid residues 115-126 of mature human P-Selectin Glycoprotein Ligand 1. Preferably, the antibody binds specifically to amino acid residues 117-123. More preferably, it binds specifically to amino acid residues 119-121, a consensus sequence among all tested epitopes. Indeed, mutation of one or more of these three amino acid residues abolishes antibody binding. In one example, this antibody, upon binding to P-Selectin Glycoprotein Ligand 1 on an activated T cell, induces the death of the activated T cell.

In one embodiment, one of the two antibodies mentioned immediately above is formed by a light chain and a heavy chain that contain, respectively, SEQ ID NOs: 1-3 and SEQ ID NOs: 4-6 (e.g., SEQ ID NOs: 19 and 20, or SEQ ID NOs: 25 and 26).

In a further aspect, the invention features a method of inducing death of an activated T cell. The method includes contacting one of the three antibodies described above with an activated T cell, in which binding of the antibody to the activated T cell induces cell death.

The invention also features a method of modulating a T cell-mediated immune response in a subject. The method includes (1) identifying a subject having or as being at risk of having a condition related to an excessive T cell-mediated immune response and (2) administering to the subject an effective amount of one of the three antibodies described above. An "excessive T cell-mediated immune response" refers to a response caused by an excessive level of activated T cells. An excessive level refers to (1) a level higher than a normal level, and (2) a level higher than desired in an individual, even though it is not greater than a normal level. Examples of the condition include an inflammatory disease, an autoimmune disease, an allergic disease, or a T cell cancer, as well as the situation in which a subject has received or is contemplated to receive an allogeneic or xenogeneic transplant.

The details of one or more embodiments of the invention are set forth in the accompanying description below. Other features, objects, and advantages of the invention will be apparent from the detailed description.

DETAILED DESCRIPTION

This invention is based, at least in part, on an unexpected discovery that activated T cells can be induced to undergo apoptosis and be depleted by binding of antibodies or their derivatives to PSGL-1 on the activated cells. The antibodies and derivatives are useful for treating conditions associated with an excessive or unwanted T cell-mediated immune response or T cell proliferation.

Accordingly, the invention features polypeptides that contain immunoglobulin light or heavy chain CDRs of anti-PSGL-1 antibodies, as well as nucleic acids encoding them. Both the immunoglobulin chains and nucleic acids can be used to make the above-mentioned antibodies and derivatives.

An immunoglobulin chain of the invention can be obtained as a synthetic polypeptide or a recombinant polypeptide. To prepare a recombinant polypeptide, a nucleic acid encoding it can be linked to another nucleic acid encoding a fusion partner, e.g., Glutathione-S-Transferase (GST), 6×-His epitope tag, M13 Gene 3 protein, or an immunoglobulin heavy chain constant region. The resultant fusion nucleic acid can be introduced to a cell for protein expression. The fusion protein can be isolated from the host cell by methods well known in the art. The isolated fusion protein can be further treated, e.g., by enzymatic digestion, to remove the fusion partner and obtain the recombinant polypeptide of interest. Alternatively, an immunoglobulin chain can be obtained from a suitable host cell by activating endogenous expression of a nucleic acid encoding the chain.

The amino acid composition of an immunoglobulin chain of the invention may vary without disrupting the ability of forming an antibody capable of binding to PSGL-1. For example, such a variant can contain one or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a polypeptide is preferably replaced with another amino acid residue from the same side chain family. Alternatively, mutations can be introduced randomly along all or part of a polypeptide of this invention, such as by saturation mutagenesis, and the resultant mutants can be screened for the ability of forming an antibody capable of binding to PSGL-1 to identify variants of this invention as described below in the examples. Thus, as an example, the term "an immunoglobulin chain containing SEQ ID NO: 19" covers immunoglobulin chains containing variants of SEQ ID NO: 19.

The above-described immunoglobulin chains and variants can be used to make an antibody of this invention or its derivatives. An "antibody" includes intact molecules as well as fragments thereof, such as Fab, F(ab')$_2$, Fv, scFv (single chain antibody), and dAb (domain antibody; Ward, et. al. (1989) *Nature*, 341, 544). A derivative of an antibody refers to a protein or a protein complex having a polypeptide variant of this invention. An antibody or derivative of this invention can be made by co-expressing corresponding light and heavy chain CDRs-containing polypeptides in a suitable host cell as described in the examples below. Alternatively, they can be made by methods known in the art of making monoclonal and polyclonal antibodies and fragments. See, e.g., Harlow and Lane (1988) *Antibodies: A Laboratory Manual*, Cold Spring Harbor Laboratory, New York.

To make an antibody of this invention, PSGL-1 or its antigenic fragment can be coupled to a carrier protein, such as KLH, mixed with an adjuvant, and injected into a host animal. Antibodies produced in that animal can then be purified by peptide affinity chromatography. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Useful human adjuvants include BCG (bacille Calmette-Guerin) and *Corynebacterium parvum*.

Polyclonal antibodies, heterogeneous populations of antibody molecules, are present in the sera of the immunized subjects. Monoclonal antibodies, homogeneous populations of antibodies to a particular antigen, can be prepared using standard hybridoma technology. See, e.g., Kohler et al.

(1975) *Nature* 256, 495; Kohler et al. (1976) *Eur. J. Immunol.* 6, 511; Kohler et al. (1976) *Eur. J. Immunol.* 6, 292; and Hammerling et al. (1981) *Monoclonal Antibodies and T Cell Hybridomas*, Elsevier, N.Y. In particular, monoclonal antibodies can be obtained by any technique that provides for the production of antibody molecules by continuous cell lines in culture such as described in U.S. Pat. No. 4,376,110; the human B-cell hybridoma technique (Kosbor et al. (1983) *Immunol Today* 4, 72; Cole et al. (1983) *Proc. Natl. Acad. Sci. USA* 80, 2026) and the EBV-hybridoma technique (Cole et al. (1983) *Monoclonal Antibodies and Cancer Therapy*, Alan R. Liss, Inc., pp. 77-96). Such antibodies can be of any immunoglobulin class including IgG, IgM, IgE, IgA, IgD, and any subclass thereof. The hybridoma producing the monoclonal antibodies of the invention may be cultivated in vitro or in vivo. The ability to produce high titers of monoclonal antibodies in vivo makes it a particularly useful method of production.

In addition, techniques developed for the production of "chimeric antibodies" can be used. See, e.g., Morrison et al. (1984) *Proc. Natl. Acad. Sci. USA* 81, 6851; Neuberger et al. (1984) *Nature* 312, 604; and Takeda et al. (1984) *Nature* 314, 452. A chimeric antibody is a molecule in which different portions are derived from different animal species, such as those having a variable region derived from a murine monoclonal antibody and a human immunoglobulin constant region. Alternatively, techniques described for the production of single chain antibodies (U.S. Pat. Nos. 4,946,778 and 4,704,692) can be adapted to produce a phage library of single chain Fv antibodies. Single chain antibodies are formed by linking the heavy and light chain fragments of the Fv region via an amino acid bridge. Moreover, antibody fragments can be generated by known techniques. For example, such fragments include, but are not limited to, $F(ab')_2$ fragments that can be produced by pepsin digestion of an antibody molecule, and Fab fragments that can be generated by reducing the disulfide bridges of $F(ab')_2$ fragments. Antibodies can also be humanized by methods described in the examples below or known in the art. For example, monoclonal antibodies with a desired binding specificity can be commercially humanized (Scotgene, Scotland; and Oxford Molecular, Palo Alto, Calif.). Fully humanized antibodies, such as those expressed in transgenic animals are within the scope of the invention (see, e.g., Green et al. (1994) *Nature* Genetics 7, 13; and U.S. Pat. Nos. 5,545,806 and 5,569,825).

Also within the scope of this invention is a method of inducing death of activated T cells, e.g., by contacting activated T cells with an antibody of the invention in vitro, and by administering to a subject in need thereof an effective amount of the antibody. Subjects to be treated can be identified as having or being at risk for having a condition related to an excessive or unwanted T cell-mediated immune response, e.g., patients suffering from autoimmune diseases, transplant rejection, allergic diseases, or T cell-derived cancers. This method can be performed alone or in conjunction with other drugs or therapy.

The term "treating" refers to administration of a composition to a subject with the purpose to cure, alleviate, relieve, remedy, prevent, or ameliorate a disorder, the symptom of the disorder, the disease state secondary to the disorder, or the predisposition toward the disorder. An "effective amount" is an amount of the composition that is capable of producing a medically desirable result in a treated subject.

Exemplary diseases to be treated include diabetes mellitus, arthritis (including rheumatoid arthritis, juvenile rheumatoid arthritis, osteoarthritis, and psoriatic arthritis), multiple sclerosis, encephalomyelitis, myasthenia gravis, systemic lupus erythematosus, autoimmune thyroiditis, dermatitis (including atopic dermatitis and eczematous dermatitis), psoriasis, Sjogren's Syndrome, Crohn's disease, aphthous ulcer, iritis, conjunctivitis, keratoconjunctivitis, type I diabetes, inflammatory bowel diseases, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, interstitial lung fibrosis, graft-versus-host disease, cases of transplantation (including transplantation using allogeneic or xenogeneic tissues) such as bone marrow transplantation, liver transplantation, or the transplantation of any organ or tissue, allergies such as atopic allergy, AIDS, and T cell neoplasms such as leukemias or lymphomas.

In one in vivo approach, a therapeutic composition (e.g., a composition containing an antibody of the invention) is administered to the subject. Generally, the antibody is suspended in a pharmaceutically-acceptable carrier (e.g., physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily.

The dosage required depends on the choice of the route of administration; the nature of the formulation; the nature of the subject's illness; the subject's size, weight, surface area, age, and sex; other drugs being administered; and the judgment of the attending physician. Suitable dosages are in the range of 0.01-100.0 mg/kg. Variations in the needed dosage are to be expected in view of the variety of compositions available and the different efficiencies of various routes of administration. For example, oral administration would be expected to require higher dosages than administration by intravenous injection. Variations in these dosage levels can be adjusted using standard empirical routines for optimization as is well understood in the art. Encapsulation of the composition in a suitable delivery vehicle (e.g., polymeric microparticles or implantable devices) may increase the efficiency of delivery, particularly for oral delivery.

Also within the scope of this invention is a pharmaceutical composition that contains a pharmaceutically-acceptable carrier and an effective amount of an antibody of the invention. The pharmaceutical composition can be used to treat diseases described above. The pharmaceutically-acceptable carrier includes a solvent, a dispersion medium, a coating, an antibacterial and antifungal agent, and an isotonic and absorption delaying agent.

The pharmaceutical composition of the invention can be formulated into dosage forms for different administration routes utilizing conventional methods. For example, it can be formulated in a capsule, a gel seal, or a tablet for oral administration. Capsules can contain any standard pharmaceutically-acceptable materials such as gelatin or cellulose. Tablets can be formulated in accordance with conventional procedures by compressing mixtures of the composition with a solid carrier and a lubricant. Examples of solid carriers include starch and sugar bentonite. The composition can also be administered in a form of a hard shell tablet or a capsule containing a binder, e.g., lactose or mannitol, a conventional filler, and a tableting agent. The pharmaceutical composition can be administered via the parenteral route. Examples of parenteral dosage forms include aqueous solutions, isotonic saline or 5% glucose of the active agent, or other well-known pharmaceutically-acceptable excipient. Cyclodextrins, or other solubilizing agents well known to those familiar with the art, can be utilized as pharmaceutical excipients for delivery of the therapeutic agent.

The efficacy of a composition of this invention can be evaluated both in vitro and in vivo. See, e.g., the examples below. Briefly, the composition can be tested for its ability to induce death of activated T cells in vitro. For in vivo studies, the composition can be injected into an animal (e.g., a mouse model) and its therapeutic effects are then accessed. Based on the results, an appropriate dosage range and administration route can be determined.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

EXAMPLE 1

Mouse Monoclonal Antibodies 15A7, 43B6, and 9F9

Generation of Anti-PSGL-1 Antibodies

Standard techniques were used to generate mouse monoclonal antibodies that specifically bound to human PSGL-1 (hCD162). More specifically, mice were immunized with membrane fraction of PHA-activated human T cells and sacrificed to generate hybridoma cell lines. Supernatants from resultant hybridoma cell lines were screened for binding to CHO cells that stably expressed hCD162. Those lines producing antibodies that bound to hCD162-expressing CHO cells, but not the parental CHO cells, were identified, subcloned, and further analyzed as described below.

Among the lines identified were m152-15A7, m166-43B6, and m128-9F9. They produced IgG1 antibodies 15A7, 43B6, and 9F9, respectively. Immunoblotting assay showed that these three antibodies pulled down from lysate of activated T-cells a protein that could be detected by anti-hCD162 antibody (kp1-1, PharMingen, San Diego, Calif.).

The just-described three antibodies were tested for their abilities to induce apoptosis of activated T cells. Culture supernatants containing monoclonal antibodies secreted by the three hybridoma cell lines were respectively incubated with either non-activated human T cells (Day 0) or in vitro activated human T cells (Day 7) for 6 hours. The cells were then stained with annexin V and subjected to FACS analysis. CD3-positive cells were gated to ensure counting of either in vitro activated human T cells or resting human T cells. The apoptotic cells were annexin V staining-positive. Table 1 summarizes the percentage of apoptotic T cells among all of the T cells scanned.

TABLE 1

Percentage of apoptotic T cells

|  | Untreated | Anti-myc | m128-9F9 | Un-treated | Anti-myc | m152-15A7 | M166-43136 |
| --- | --- | --- | --- | --- | --- | --- | --- |
| Day 0 | 4.17 | 6.67 | 5.82 | 18.18 | 15.52 | 5.23 | 6.57 |
| Day 7 | 12.63 | 13.36 | 28.71 | 24.18 | 23.08 | 51.66 | 49.44 |

These results indicate that mouse 15A7, 43B6, and 9F9 antibodies (1) are hCD162-specific and (2) can bind to human activated T cells and induce apoptosis of activated T cells, but not resting human T cells.

Apoptosis assay was also conducted on PHA-activated human peripheral blood mononuclear cells (PBMC). It was found that the antibodies only induced apoptosis in activated T cells, but not in resting T cells, B cells, or in neutrophils.

It is known that T cell-depleting antibodies, such as anti-CD3, are able to induce production of soluble factors. Therapy using such antibodies usually results in a deleterious cytokine syndrome. To test if anti-PSGL-1 antibody also caused cytokine-associated side effects, freshly isolated human PBMC were cultured with 15A7 for 24, 48, or 72 hours. The levels of cytokines in the supernatant were then determined. Considerable amounts of IL-2, TNF-α, and IFN-γ were produced in PHA-activated PBMC (positive control), while levels of these cytokines from 15A7-treated cells were not detectable. These results supported that anti-PSGL-1 has no or little effect on resting peripheral blood cells, in both aspects of apoptotic induction and cell activation.

Since the above-described antibodies selectively induce apoptosis of activated T cells without causing adverse effects on resting T or other immune cells, administration of them to a subject is unlikely to result in lymphopenia or broad immunodeficiency like anti-CD3 or immunosuppressant does.

Epitope Mapping of Anti-CD 162 Antibodies

To map the binding epitopes of mouse 15A7, 43B6, and 9F9 on human CD162, a series of fusion proteins covering various regions of human CD162 were expressed and purified. Interactions between the fusion proteins and these monoclonal antibodies were examined by sandwich enzyme-linked immunosorbent assay (ELISA).

Briefly, fragments covering various regions of human CD 162 gene were expressed as fusion proteins with human immunoglobulin gamma 1 heavy chain constant region in *E. coli*. cDNA encoding the human immunoglobulin gamma 1 heavy chain constant region was amplified by PCR with primers having a BglII site and a BamHI site. The PCR product was cut by BglII and BamHI, and subcloned into a pET-32a vector (Novagen®) that had been digested by the same enzymes. Then, cDNAs encoding various regions of hCD162 were amplified by PCR with primers having an NdeI site at the 5' end and a BglII site at the 3' end. The PCR products were cut by the corresponding enzymes and in frame fused to the sequence encoding the human immunoglobulin gamma 1 heavy chain constant region in the pET-32a vector. Primers used in each construction are listed in Table 2, and the sequences of the primers are listed in Table 3.

TABLE 2

Names of primers used in each experiment

| For amplifying sequences encoding: | Forward primer | Reverse primer |
| --- | --- | --- |
| *E. coli* expressed hCD162 fragments | | |
| 42-119 | AB1001 | AB1005 |
| 42-80 | AB1001 | AB1008 |
| 61-99 | AB1003 | AB1009 |
| 81-119 | Ab1004 | AB1005 |
| 42-70 | AB1001 | AB1007 |
| 42-60 | AB1001 | AB1006 |
| 50-80 | AB1002 | AB1008 |
| 50-70 | AB1002 | Ab1007 |

TABLE 2-continued

Names of primers used in each experiment

| For amplifying sequences encoding: | Forward primer | Reverse primer |
|---|---|---|
| 42-319 | AB1001 | Ab1010 |
| 115-126 | AB1022 | AB1023 |
| 115-126EtoR | AB1024 | AB1025 |
| V region of cDNAs | | |
| light chain | AB1058 | AB1059 |
| heavy chain | AB1058 | AB1060 |
| Mammalian expressed hCD162 fragments | | |
| 1-119 | AB1011 | AB1013 |
| 1-319 | AB1011 | AB1012 |
| 110-319 | AB1058 | AB1059 |
| 94-148 | AB1020 | AB1021 |
| 119-222 | AB1018 | AB1019 |
| 174-269 | AB1016 | AB1017 |
| 214-317 | AB1014 | AB1015 |
| Chimeric chains | | |
| 15A7 light chain | AB1030 | AB1031 |
| 15A7 heavy chain | AB1032 | AB1033 |
| 9F9 light chain | AB1026 | A131027 |
| 9F9 heavy chain | AB1028 | AB1029 |
| 43B6 light chain | AB1034 | AB1035 |
| 43B6 heavy chain | AB1036 | AB1037 |
| Humanized chains | | |
| 15A7 light chain | AB1048 | AB1057 |
| 15A7 light chain 1st pair | AD1049 | AB1050 |
| 15A7 light chain 2nd pair | AB1051 | AB1052 |
| 15A7 light chain 3rd pair | AB1053 | AB1054 |
| 15A7 light chain 4th pair | AB1055 | Ab1056 |
| 15A7 heavy chain | AB1038 | AB1047 |
| 15A7 heavy chain 1st pair | AB1039 | AB1040 |
| 15A7 heavy chain 2nd pair | AB1041 | AB1042 |
| 15A7 heavy chain 3rd pair | AB1043 | AB1044 |
| 15A7 heavy chain 4th pair | AB1045 | AB1046 |

TABLE 3

Primer sequences

| Name | Sequence | SEQ ID NO: |
|---|---|---|
| AB1001 | cccgggacCATATGcaggccaccgaatatgagtacc | 39 |
| AB1002 | tatgagCATATGgattatgatttcctgccagaaacgg | 40 |
| AB1003 | aaacggagCATATGgaaatgctgaggaacagcactgacacc | 41 |
| AB1004 | aaccctCATATGaccactgtggagcctgctgcaaggcg | 42 |
| AB1005 | gtggtcAGATCTtccatagctgctgaatccgtggacagg | 43 |
| AB1006 | GTTCCTCAGATCTTCTGGAGGCTCCGTTTCTGGCAGG | 44 |
| AB1007 | AGGCCCAAGATCTGGAGTGGTGTCAGTGCTGTTCCTC | 45 |
| AB1008 | ggctccAGATCTgtagactcaggggttccaggccc | 46 |
| AB1009 | gtggtcAGATCTgtgactgcccctcctgcatccaggcc | 47 |
| AB1010 | GCCAGCAGATCTTGCTTCACAGAGATGTGGTCTGGGG | 48 |
| AB1011 | cgcggatccatgcctctgcaactcctcctgttgc | 49 |
| AB1012 | GCCAGCCTCGAGCTTCACAGAGATGTGGTCTGGGG | 50 |
| AB1013 | GGTCTGctcgagCATAGCTGCTGAATCCGTGGACAGGTTC | 51 |
| AB1061 | agacaggccaccgaagggaacctgtccacg | 52 |
| AB1062 | cgtggacaggttcccttcggtggcctgtct | 53 |
| AB1014 | ccgctcgagcgccaagattaggatggc | 54 |
| AB1015 | cgggatccactcaaaccacagccatgg | 55 |
| AB1016 | ccgctcgagtggtagtaggttccatgg | 56 |
| AB1017 | cgggatcaactcaacccacaggcctg | 57 |
| AB1018 | ctgtgcctcgagggctgtggtttgagtg | 58 |
| AB1019 | cgggatccatggagatacagaccactcaac | 59 |
| AB1020 | cgggatccgatgcaggaggggcagtcac | 60 |

TABLE 3-continued

Primer sequences

| Name | Sequence | SEQ ID NO: |
|---|---|---|
| AB1021 | ggccgtcactcgagttgtctgtgcctc | 61 |
| AB1022 | TatgGATTCAGCAGCTATGGAGATACAGACCACTCAACCAgcA | 62 |
| AB1023 | GATCTgcTGGTTGAGTGGTCTGTATCTCCATAGCTGCTGAATCCA | 63 |
| AB1024 | TatgGATTCAGCAGCTATGCGGATACAGACCACTCAACCAgcA | 64 |
| AB1025 | GATCTgcTGGTTGAGTGGTCTGTATCCGCATAGCTGCTGAATCCA | 65 |
| AB1026 | CTAGTCTAGATGACCCAAACTCCACTCTCCC | 66 |
| AB1027 | CTAGTCTAGAATTAGGAAAGTGCACTTAGCATCAGCCCGTTTGATTTCC | 67 |
| AB1028 | TAACATtctagATGCTGTTGGGGCTGAAGTGGG | 68 |
| AB1029 | GGATAGTCTAGAGGTTGTGAGGACTCACCTGAGGAGACGGTGACCGTGG | 69 |
| AB1030 | CTAGTCTAGATGGAGACAGACACACTCCTGTTATGGG | 70 |
| AB1031 | CTAGTCTAGAATTAGGAAAGTGCACTTTTTCCAGCTTGGTCCCCCCTCC | 71 |
| AB1032 | CTAGTCTAGATGGACTCCAGGCTCAATTTAGTTTTCC | 72 |
| AB1033 | CTAGTCTAGAGGTTGTGAGGACTCACCTGAGGAGACGGTGACTGAGGttcc | 73 |
| AB1034 | CTAGTCTAGATGGATTTTCTGGTGCAGATTTTCAGC | 74 |
| AB1035 | CTAGTCTAGAATTAGGAAAGTGCACTTAGCATCAGCCCGTTTCAGCTCC | 75 |
| AB1036 | CTAGTCTAGATGGAATGGAGCTGGGTCTTTCTC | 76 |
| AB1037 | CTAGTCTAGAGGTTGTGAGGACTCACCAGCTTCCAGTGGATAGACTGATGG | 77 |
| AB1038 | TCTATCTAGATGAACTTCGGGTCCAGCTTGATTTTCCTTGTCCTTGTTTTAAAAGGTGTCCAGTG | 78 |
| AB1039 | CCTTGTTTTAAAAGGTGTCCAGTGT-GAAGTGCAACTGGTGGAGTCTGGGGGAGGCTTAGTGCAGCCTGG | 79 |
| AB1040 | CTGAAAGTGAATCCAGAGGCTGCACAGGAGAGTCTCAAGCTTCCTCCAGGCTGCACTAAGCCTCC | 80 |
| AB1041 | GCCTCTGGATTCACTTTCAGTAGCTTTG-GAATGCACTGGGTTCGCCAGGCTCCAGGGAAGGGACTCGAG | 81 |
| AB1042 | GCATAGAAGATGGTACTACTGCCACCATTAATGTATGCGACCCACTCGAGTCCCTTCCCTGGAGCC | 82 |
| AB1043 | GTAGTACCATCTTCTATGCAAACGCAGTGAAGGGCCGATTCACCATCTCCAGAGATAATGCC | 83 |
| AB1044 | CCTCAGCCCTCAGAGAATTCATTTGCAGGTACAGGGTGTTCTTGGCATTATCTCTGGAGATGG | 84 |
| AB1045 | GAATTCTCTGAGGGCTGAGGACACGGCCGTGTATTACTGTGCAAGATATGCTAGTTACGGAGG | 85 |
| AB1046 | CTGTGACCAGGGTGCCTTGGCCCCAATAGTCCATAGCACCCCCTCCGTAACTAGCATATC | 86 |
| AB1047 | ACCCTCTAGAGGTTGTGAGGACTCACCTGAGGAGACTGTGACCAGGGTGCCTTGGCC | 87 |
| AB1048 | TCTATCTAGATGGAGACAGACACAATCCTGCTATGGGTGCTGCTGCTCTGGGTTCCAGGC | 88 |
| AB1049 | GCTGCTCTGGGTTCCAGGCTCCACTGGTGACATTCAGATGACCCAATCTCCGAGCTCTTTG | 89 |
| AB1050 | GATCTGCAGGTGATAGTGACCCTATCCCCTACAGACGCAGACAAAGAGCTCGGAGATTGG | 90 |

TABLE 3-continued

Primer sequences

| Name | Sequence | SEQ ID NO: |
|---|---|---|
| AB1051 | CACTATCACCTGCAGATCTAGTCAGAGCATTGTACATAATGATGGAAACAC CTATTTTGAATG | 91 |
| AB1052 | GATGAGAAGCTTGGGTGCCTTTCCTGGTTTCTGTTGGTACCATTCAAAATA GGTGTTTC | 92 |
| AB1053 | GCACCCAAGCTTCTCATCTATAAAGTTTCCAATCGATTTTCTGGTGTCCCA TCCAGGTTTAGTGGC | 93 |
| AB1054 | GCAGAGAAGAGATGGTGAGGGTGAAGTGTGTCCCAGACCCACTGCCACTAA ACCTGGATGG | 94 |
| AB1055 | CTCACCATCTCTTCTCTGCAGCCGGAGGATTTCGCAACCTATTACTGTTTT CAAG | 95 |
| AB1056 | CCTTGGTGCCTTGACCGAACGTGAGAGGAACATATGAACCTTGAAAACAGT AATAGG | 96 |
| AB1057 | ACCCTCTAGAATTAGGAAAGTGCACTTACGTTTGATTTCCACCTTGGTGCC TTGACCG | 97 |
| AB1058 | TATATCTAGAATTCCCCCCCCCCCCCCCC | 98 |
| AB1059 | TATAGAGCTCAAGCTTGGATGGTGGGAAGATGGATACAGTTGGTGC | 99 |
| AB1060 | TATAGAGCTCAAGCTTCCAGTGGATAGAC(C/A/T)GATGGGG(C/G) TGT(C/T)GTTTTGGC | 100 |

The above-described expression constructs were transformed into *Escherichia coli* strain BL21 (DE3). The transformed cells were harvested after 6 hours of IPTG (2 mM) induction and resuspended in PBS. After the cells were sonicated and spun down at 14,000 g for 10 minutes, the resultant supernatants were collected for purification of the fusion proteins. More specifically, the supernatants were first incubated with protein G or protein A beads for 3 hours at 4° C. The beads were then spun down at 3,000 g and washed with washing buffer I (0.05% Triton® X-100, 50 mM Tris-HCl, pH 8.5, 400 mM NaCl, 1 mM CaCl$_2$ and 1 mg/ml OVA) and washing buffer II (0.05% Triton® X-100, 50 mM Tris-HCl, pH 8.5 and 1.50 mM of NaCl) for 5 times each. Bound proteins were then eluted with an elution buffer containing 0.1 M of glycine-HCl, pH 2.7 and neutralized with 1 M Tris-HCl, pH 8.6. All purified fusion proteins were quantified by Bio-Rad® protein assay (Bio-Rad® Laboratories, Cat. No. 500-0006) and verified by SDS-PAGE.

A sandwich ELISA was conducted to study the interaction between the hCD162 fragments and each of 15A7, 9F9, and 43B6. 96-well microtiter plates were coated with goat anti-human IgG (Southern Biotechnology, Cat. No. 2040-01) antibody (2 µg/ml, 50 µl/well) overnight at 4° C. Plates were blocked by incubation with 0.25% of BSA in PBS (150 µl/well) for 1 hour at 37° C. The blocked plates were then incubated with fusion proteins containing various fragments of human CD162 (2 µg/ml) for 2 hours at room temperature. After washing 4 times with PBS containing 0.05% of Tween®20 (PBST), the plates were incubated with testing antibodies (2 µg/ml) for 1.5 hours at room temperature. After incubation, the plates were washed 4 times with PBST. 50 µl of 1 to 3000 diluted goat anti-mouse IgG conjugated with alkaline phosphatase (Southern Biotechnology, Cat. No. 1031-04) was then added to each well and the plates were incubated for 1 hour at 37° C. Enzyme reaction was carried out by adding 50 µl of an alkaline phosphatase substrate solution (1 alkaline phosphatase substrate tablet dissolved in 5 ml of substrate buffer containing 0.012 M of Na$_2$CO$_3$, 0.16 M of NaHCO$_3$ and 1 mM of MgCl$_2$ at pH 8.6), and absorbance at 405 nm was determined.

It was found that 43B6 and 9F9 were able to interact with all fusion proteins containing residues 50 to 60 of mature human CD162, indicating that epitopes of 43B6 and 9F9 were located between residues 50-60. Unlike 9F9 and 43B6, 15A7 only bound to the fusion protein covering residues 42 to 319, but not the fusion protein covering residues 42-119, indicating that the epitope of 15A7 was located between residues 119 to 319. The location of the epitope of 15A7 was then narrowed down to between residues 115 to 126. Change of one amino acid at position 120 (Glu→Arg) diminished interaction between 15A7 and the fusion protein, indicating that the primary contacting domain of 15A7 on human CD162 is located at or adjacent to position 120, and the residue Glu is essential for the interaction.

Fusion proteins covering various human CD162 regions were also expressed in mammalian cells and were tested for their interaction with 15A7. Fragments covering these regions were expressed as fusion proteins with human immunoglobulin gamma 1 heavy chain constant region in mammalian cells. First, the cDNA encoding human immunoglobulin gamma 1 heavy chain constant region was inserted into a pcDNA3 vector (Invitrogen). Second, cDNAs encoding various regions of hCD162 were amplified by PCR with primers introducing a BamHI site at the 5' end and an XhoI site at the 3' end. These PCR products were cut by the corresponding enzymes and subcloned into the human immunoglobulin gamma 1 heavy chain constant region-containing pcDNA3 vector. The name and sequence for each primer are listed in Tables 2 and 3 above.

The just-described mammalian expression vectors were transiently transfected into COS-7 cells by Lipofectamine™ 2000 (Invitrogen™, Cat. No. 11668-027) following manufacturer's guide. The transfected cells were grown in ultra low-Ig medium (Invitrogen™, Cat. No. 16250-078). The expressed proteins were purified and subjected to sandwich ELISA in the same manner described above.

The ELISA results show that only the fusion proteins containing residues 94 to 148 were able to interact with 15A7. These results are consistent with the idea that the epitope of 15A7 is located between residues 115 to 126.

All of the above results indicate that the epitopes of 9F9, 43B6, and 15A7 are protein-dependent, instead of carbohydrate modification-dependent, since all three antibodies bind bacterially expressed fusion proteins. They also indicate that, although 15A7, 9F9, and 43B6 show similar properties in term of binding specificity and function of inducing apoptosis in activated T cells, they function through different domains of human CD162 and behave differently.

EXAMPLE 2

Chimeric Antibodies 15A7, 43B6, and 9F9

Cloning of Light and Heavy Chain Variable Regions of Anti-CD162 Antibodies cDNAs encoding the light and heavy chain variable regions ($V_L$ and $V_H$) of antibodies 15A7, 43B6, and 9F9 were amplified by an anchored PCR method. The 3' primers hybridized to the C regions and the 5' primers hybridized to G tails attached to the cDNA using terminal deoxytransferase. The PCR fragments were cloned into a pCRII vector (Invitrogen™). Several independent clones for each chain were sequenced and compared. A sequence represented by the majority of the independent clones was picked. The translated amino acid sequence was then analyzed to confirm that the chosen sequence possessed the characteristics of typical mouse light or heavy chain V region, and belonged to a specific subtype. The complementarity determining regions (CDRs) were then identified by comparing the translated amino acid sequences with consensus sequence of each subtype. The name and sequence for each primer used are listed in Tables 2 and 3 above. The deduced amino acid sequences of the light and heavy chain V regions of 15A7, 43B6, and 9F9 (SEQ ID NOs: 19-24) are shown in Summary.

Chimeric Antibodies

To generate vectors for expressing chimeric antibodies, cDNAs encoding the $V_L$ and $V_H$ regions of 15A7, 43B6, and 9F9 were amplified by PCR using primers to include the 5' signal peptide sequence and the 3' splice donor signal. The primers also introduced XbaI sites at both ends of the PCR products, which were then cut by XbaI enzyme and ligated into XbaI-digested pVκ, pVg1, pVg2, or pVg4 vector. More specifically, the $V_L$ region cDNAs of 15A7, 43B6, and 9F9 were subcloned into the plasmid pVκ. This plasmid contained a CMV promoter, and a sequence encoding the human light chain constant region. The $V_H$ region cDNAs of 15A7, 43B6 and 9F9 were subcloned into plasmids pVg1, pVg2, or pVg4. Each of the three plasmids had a CMV promoter. They also contained, respectively, the human heavy chain constant regions of IgG1, IgG2, and IgG4.

Each of the above-described light chain-encoding plasmids was co-transfected with a heavy chain-encoding plasmid into COS-7 cells. The supernatants of the transfected cells were collected. Chimeric antibodies in the supernatants were analyzed for the ability to bind to human CD162 and to induce apoptosis of activated T cells.

It was found that all chimeric antibodies made from 15A7, 43B6, and 9F9 bound to Sp2/0 transfectants stably expressing human CD162, but not to parental Sp2/0 cells, indicating that they retained the human CD162-binding ability specificity. Furthermore, it was found that the chimeric antibodies induced apoptosis in T cells that had been activated for 7 days, indicating that they retained this function of their mouse counterparts as well.

Humanized Antibodies

Mouse 15A7 was used to make humanized antibodies by grafting its CDRs onto a human framework. To retain binding affinity and specificity, it is essential to conserve the V region conformation when grafting the CDRs onto the human framework. To select a proper framework donor, the amino acid sequences of mouse 15A7 light and heavy chain V regions were compared with those of 50 mouse antibodies that had been humanized.

It was found that a mouse antibody, mDREG-55, had high sequence homology to mouse 15A7 V region in both light and heavy chains. Listed below is a sequence alignment of mouse 15A7 against this mDREG-55 antibody (CDRs are highlighted):

```
Light chain alignment:
mDREG-55      DIVLTQSPASLSVSLGERASISCKASQSVDYDGDSYMNWYQQKPGQPPKLLIYAASNLES
              DI++TQ+P  SL VSLG++ASISC++SQS+ + DG++Y  WY QKPGQ PKLLIY   SN  S
m15A7         DILMTQTPLSLPVSLGDQASISCRSSQSIVHNDGNTYFEWYLQKPGQSPKLLIYKVSNRFS mDREG-55      GIPARFSGSGSGTDFTLNIHPVEEEDAATYYCQQSNEDPWTFGGGTKLEIK              SEQ ID NO: 33
              G+P RFSGSGSGT FTLNI  VE ED   YYC Q +  P TF GGTKLE+K
m15A7         GVPDRFSGSGSGTHFTLNISRVEAEDLGIYYCFQGSYVPLTFGAGTKLELK              SEQ ID NO: 34

Heavy chain alignment:
MDREG-55      EVKLVESGGGLVKPGGSLKLSCAASGFTFSTYAMSWVRQTPEKRLEWVASISTGGSTYYPDSVKG
              +V+LVESGGGLV+PGGS KLSCAASGFTFS++ M WVRQ PEK LEWVA I+ G ST +Y ++VKG
m15A7         DVQLVESGGGLVQPGGSRKLSCAASGFTFSSFGMHWVRQAPEKGLEWVAYINGGSSTIFYANAVKG MDREG-55      RFTISRDNARNILYLQMSSLRSEDTAMYYCARDYDGYFDYWGQGTTLTVSS              SEQ ID NO: 35
              RFTISRDN +N L+LQM+ LRSEDTA+YYC R   Y  G  DYWGQGT++TVSS
m15A7         RFTISRDNPKNTLFLQMTILRSEDTAIYYCGRYASYGGGAMDYWGQGTSVTVSS             SEQ ID NO: 36
```

Mouse DREG-55 is a monoclonal IgG1 antibody against L-selectin. The sequences of mouse 15A7 $V_L$ and $V_H$ regions were respectively 64.3% (framework only: 73.8%) and 70% (framework only: 81.6%) homologous to those of mouse DREG55. Humanized DREG-55 (HuDREG-55) had been constructed using framework sequences of $V_L$ and $V_H$ regions from a human antibody Gal. Therefore, to humanize mouse 15A7, the framework sequences of human Gal light and heavy chains were used to replace the counter parts of mouse 15A7.

The humanized 15A7 light and heavy variable regions were each assembled by 4 pairs of synthetic oligonucleotides (~80 bases in length). The oligonucleotides of each pair were overlapped by around 20 nucleotides. Nucleotide sequences were selected and synthesized to encode the protein sequences of the humanized variable regions including signal peptides. The assembling and amplification of the genes were conducted in four steps: (1) the four pairs of complementary oligonucleotides were annealed and extended with Klenow fragment in 4 separate reactions; (2) the resulting 4 dsDNA fragments were mixed pair wise, denatured, reannealed, and extended in two separate reactions; (3) the resulting two dsDNA fragments were mixed, denatured, reannealed, and extended to create the final full-length dsDNA; and (4) the resulting DNA was amplified by PCR with primers to introduce an XbaI site at both ends. The PCR fragment was then cut by XbaI and inserted into the respective XbaI-digested pVκ and pVg4 vectors. Then, at positions where the interactions between CDR and the framework were considered important, the Ga1's residues were changed back into those of the mouse 15A7 (i.e., I62V and D74H). Listed below are alignments of mouse 15A7 and humanized 15A7 (Hu15A7) against mDREG-55, in which V62 and H74 are underlined.

Tris-HCl, pH 8.5 and 150 mM of NaCl), the bound antibodies were eluted with an elution buffer containing 0.1 M of glycine-HCl, pH 2.7, and neutralized with 1 M Tris-HCl, pH 8.6.
Affinity Measurements Binding affinities of the above-described mouse, chimeric, and humanized 15A7 antibodies were determined by competitive binding.

Mouse 15A7 was biotinylated by an EZ-Link™ Sulfo-NHS-Biotin system (Pierce Biotechnology, Cat. No. 21217). Briefly, 0.5 mg ($3.3 \times 10^{-6}$ nmoles) of mouse 15A7 was dissolved in 187 µl of PBS and mixed with $6.8 \times 10^{-5}$ nmoles of Sulfo-NHS-Biotin. The mixture was then incubated on ice for 2 hours before free biotins were removed by dialyzing at 4° C. overnight against PBS. The Biotin-labeled mouse 15A7 thus obtained was stored at 4° C. until use.

Sp2/0 transfectants stably expressing human CD162 were used as source of human CD162 antigen. Biotin-labeled mouse 15A7 was used as tracer. Increasing amounts of competitor antibodies (mouse, chimeric, or humanized 15A7) were mixed with 35 ng of Biotin-labeled mouse 15A7 and

```
Light chain alignment:
hDREG-55     DIQMTQSPSSLSASVGDRVTITCKASQSVDY DGDSYMNWYQQKPGKAPKLLIYAASNLES
mouse 15A7   DILMTQTPLSLPVSLGDQASISCRSSQSIVHNDGNTYPEWYLQKPGQSPKLLIYKVSNRFS
Hu15A7       DIQMTQSPSSLSASVGDRVTITCRSSQSIVHNDGNTYPEWYQQKPGKAPKLLIYKVSNRFS hDREG-55     GIPSRFSGSGSGTDFTLTISSLQPEDFATYYCQQSHEDPWTFGQGTKVEIK            SEQ ID NO: 37
m15A7        GVPDRFSGSGSGTHFTLNISRVEAEDLGIYYCRQGSYVPLTFGAGTKLELK            SEQ ID NO: 34
Hu15A7       GVPSRFSGSGSGTHFTLTISSLQPEDFATYYCRQGSYVPLTFGQGTKVEIK            SEQ ID NO: 25

Heavy chain alignment:
hDREG-55     EVQLVESGGGLVQPGGSLRLSCAASGFTFSTYAMSWVRQAPGKGLEWVASISTGGST YYPDSVKG
m15A7        DVQLVESGGGLVQPGGSRKLSCAASGFTFSSFGMHWVRQAPEKGLEWVAYINGGSSTIPYANAVKG
Hu15A7       EVQLVESGGGLVQPGGSLRLSCAASGFTFSSFGMHWVRQAPGKGLEWVAYINGGSSTIPYANAVKG hDREG-55     RFTISRDNAKNTLYLQMNSLRAEDTAVYYCAR   DY DGYFDYWGQGTLVTVSS          SEQ ID NO: 38
m15A7        RFTISRDNPKNTLFLQMTILRSEDTAIYYCGRYASYGGGAMDYWGQGTSVTVSS          SEQ ID NO: 36
Hu15A7       RFTISRDNAKNTLYLQMNSLRAEDTAVYYCARYASYGGGAMDYWGQGTLVTVSS          SEQ ID NO: 26
```

Plasmids thus obtained encoded humanized 15A7 heavy and light chains. These plasmids were then co-transfected into COS-7 cells. The exhausted supernatants from cultured cells were then collected. Humanized 15A7 in the supernatants was tested for its ability to bind to CHO transfectants stably expressing hCD162 and to induce apoptosis in the T cells activated for 7 days. The results show that it retains these abilities.
Preparation of Chimeric and Humanized Antibodies Cells producing humanized and chimeric antibodies were generated. More specifically, Sp2/0 cells (Sp2/0-Ag14; ATCC CRL 1581) were stably transfected with the appropriate plasmids by electroporation using a Gene Pulser® apparatus (Bio-Rad® Laboratories) at 360 V and 25 µF capacitance according to the manufacturer's instructions. Before transfection, the plasmids were linearized by digesting with BamHI enzyme. All transfections were performed using $10^7$ cells in PBS and 20 µg each of plasmid DNA. The cells from each transfection were plated into two 96-well tissue culture plates. After 48 hours, a selective medium (DMEM 10% FBS/hypoxanthine/thymidine media supplement) and 1 µg/ml mycophenolic acid was applied. Antibody-producing cells were screened and isolated by examining the presence of antibody in the culture supernatant by ELISA.

Isolated cells were cultured in serum-free or low-Ig medium, and the cultured supernatant was collected. Antibodies were purified by passage over a column of staphylococcal protein A-Sepharose CL-4B. After washing 5 times each with washing buffer I (0.05% Triton®X-100, 50 mM Tris-HCl, pH 8.5, 400 mM NaCl, 1 mM $CaCl_2$ and 1 mg/ml OVA) and washing buffer II (0.05% Triton®X-100, 50 mM incubated with $1 \times 10^5$ CD162-expressing Sp2/0 cells for 1.5 hours at 4° C. with constant shaking. After washing, secondary antibody, Streptavidin-PE (Becton Dickinson Immunocytometry System Inc. Cat. No. 349023) was added to the mixture. After incubating for 45 minutes at 4° C., the cells were washed again, resuspended in 300 µl of PBS-1% of FBS, and subjected to FACS analysis.

It was found that the half-maximum competing concentration of mouse 15A7 was 3.72 µg/ml while those of chimeric and humanized 15A7 were around 5.71 µg/ml and 4.51 µg/ml, respectively. These results indicate that the affinities of mouse, chimeric, and humanized 15A7 are comparable. In other words, the binding affinity (Ka) for mouse 15A7 is $4.03 \times 10^7 \text{ M}^{-1}$ while those for chimeric and humanized 15A7 are $2.62 \times 10^7 \text{ M}^{-1}$ and $3.33 \times 10^7 \text{ M}^{-1}$, respectively.
Competition Analysis Competition analysis was conducted to study interaction among the above-described three mouse antibodies, PSGL-1, and P-selectin.

P-selectin is a major high-affinity ligand for PSGL-1 on most leukocytes. In order to investigate whether the three antibodies prevent binding of P-selectin to PSGL-1, binding of purified human P-selectin to activated T cells was measured in the presence of the three antibodies. KPL-1, known to block interaction of P-selectin and PSGL-1, was used as a positive control.

Human PBMC were activated with 1% PHA for 2 days and maintained in IL-2-containing medium for 3 days. The cells were incubated with titrated 9F9, 15A7, 43B6, KPL-1 (an PSGL-1 antagonist), or a control antibody (9E10) for 30 minutes, followed by the addition of recombinant human P-selectin (1.25 µg/ml). Binding of P-selectin to activated T cells was measured by anti-P-selectin-FITC analyzed on FACS.

Consistent with previous reports, KPL-1 almost completely abolished P-selectin's binding to activate T cells at a low concentration (0.31 µg/ml). 43B6 blocked binding of P-selectin to activated T cells as effectively as KPL-1 did, whereas a higher concentration of 9F9 was required to achieve the same effect. Indeed, 0.08 mg/ml KPL or 43B6 was needed to abolish 50% of the binding. In contrast, 5 µg/ml 9F9 was required. Moreover, 15A7 did not have any inhibitory effect on P-selectin binding even at 20 µg/ml. Surprisingly, it enhanced binding of P-selectin to PSGL-1. These results indicate that 15A7 and P-selectin bind to different motifs of PSGL-1 on activated T cells.

The fact that 15A7 did not compete with P-selectin for PSGL-1 indicates that in vivo administration of 15A7 is not supposed to affect innate immunity by interfering P-selectin-dependent recruitment of leukocytes.

It has been reported that PSGL-1 is expressed at low levels on platelets. The effects of 15A7 antibodies on platelets were examined. It was found that the antibodies did not enhance or inhibit aggregation of human platelets.

EXAMPLE 3

Hamster Monoclonal Antibody TAB4 Against Mouse PSGL-1

A monoclonal antibody against mouse PSGL-1, TAB4, was prepared in the manner similar to the method described in Example 1. It induced T cell apoptosis in vitro and depleted T cells in vivo. To determine if it interfered with binding between mouse PSGL-1 and mouse P-selectin, competition analysis was performed in the manner similar to the method described in Example 2. It was found that TAB4 did not inhibit mouse P-selectin binding to mouse PSGL-1 even at a concentration as high as 20 µg/ml.

EXAMPLE 4

Mouse Monoclonal Antibodies 4B7, 5C4, 12E7, 14B3, 17E5, and 18D12

Additional monoclonal antibodies against human PSGL-1, 4B7, 5C4, 12E7, 14B3, 17E5, and 18D12, were characterized. Upon binding to an activated T cell, they all induced death of the activated T cells. Competition analysis was conducted in the manner described in Example 2 to determine if they blocked interaction between PSGL-1 and P-selectin. It was found that these antibodies have little, if any, inhibitory effect on human P-selectin binding to human PSGL-1, even at the highest concentration tested (5 µg/ml).

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the invention.

What is claimed is:

1. An isolated antibody that binds specifically to human P-Selectin Glycoprotein Ligand 1 (PSGL-1) without interfering with binding between PSGL-1 and P-Selectin, wherein the antibody, upon binding to human PSGL-1 expressed on an activated T cell, induces death of the activated T cell.

2. The antibody of claim 1, wherein the antibody is a humanized antibody.

3. A composition comprising the antibody of claim 1.

4. The composition of claim 3, wherein the antibody is a humanized antibody.

* * * * *